US012584931B2

(12) United States Patent
Dei et al.

(10) Patent No.: US 12,584,931 B2
(45) Date of Patent: Mar. 24, 2026

(54) DEVICES AND CARTRIDGES FOR EXTRACTING BIO-SAMPLE REGIONS AND MOLECULES OF INTEREST

(71) Applicant: xMD Diagnostics, Inc., Baltimore, MD (US)

(72) Inventors: Ting Pau Dei, Califon, NJ (US); Stephen W. Ritterbush, Annapolis, MD (US); Benjamin Shapiro, Washington, DC (US)

(73) Assignee: XMD DIAGNOSTICS, INC., Baltimore, MD (US)

( * ) Notice: Subject to any disclaimer, the term of this patent is extended or adjusted under 35 U.S.C. 154(b) by 1011 days.

(21) Appl. No.: 17/266,531

(22) PCT Filed: Aug. 7, 2019

(86) PCT No.: PCT/US2019/045433
§ 371 (c)(1),
(2) Date: Feb. 5, 2021

(87) PCT Pub. No.: WO2020/033496
PCT Pub. Date: Feb. 13, 2020

(65) Prior Publication Data
US 2021/0318341 A1 Oct. 14, 2021

Related U.S. Application Data

(60) Provisional application No. 62/715,541, filed on Aug. 7, 2018.

(51) Int. Cl.
*G01N 35/00* (2006.01)
*B01L 3/00* (2006.01)
(Continued)

(52) U.S. Cl.
CPC ........ *G01N 35/00029* (2013.01); *B01L 3/508* (2013.01); *B01L 9/52* (2013.01);
(Continued)

(58) Field of Classification Search
None
See application file for complete search history.

(56) References Cited

U.S. PATENT DOCUMENTS 7,695,752 B2  4/2010 Bonner et al.
7,709,047 B2  5/2010 Emmert-Buck et al.
(Continued)

FOREIGN PATENT DOCUMENTS

WO 2015199976 A1 12/2015

OTHER PUBLICATIONS

International Search Report and Written Opinion dated Feb. 24, 2020, from International Patent Application No. PCT/US19/45433, 14 sheets.
(Continued)

*Primary Examiner* — Kathryn Elizabeth Limbaugh
(74) *Attorney, Agent, or Firm* — KATTEN MUCHIN ROSENMAN LLP

(57) ABSTRACT

The disclosed invention provides a cartridge, method and cartridge processing systems for molecular tests that include extracting one or more biological materials from a tissue. The cartridge includes a base having a receptacle inside the base, a lid placed over the receptacle, and a gasket in the base. The base includes a transparent window placed under the receptacle, and the receptacle contains a slide on which the tissue is disposed. A film is disposed on an inner surface of the lid, and the film is suitable to extract the one or more biological materials from the tissue. The gasket surrounds the slide, and the lid creates a sealed chamber around the gasket that encloses the slide, and vacuum suction is applied
(Continued)

through a port of the base to press the film against the tissue
on the slide.

7 Claims, 13 Drawing Sheets

(51) Int. Cl.
| | |
|---|---|
| *B01L 9/00* | (2006.01) |
| *C12M 1/00* | (2006.01) |
| *G01N 1/31* | (2006.01) |
| *G01N 35/02* | (2006.01) |

(52) U.S. Cl.
CPC ............. *C12M 23/22* (2013.01); *G01N 1/312*
(2013.01); *G01N 35/025* (2013.01); *B01L*
*2200/0689* (2013.01); *B01L 2300/0822*
(2013.01); *G01N 2035/00138* (2013.01)

(56) References Cited

U.S. PATENT DOCUMENTS

| | | | |
|---|---|---|---|
| 8,597,715 | B2 | 12/2013 | Emmert-Buck et al. |
| 2009/0225309 | A1 | 9/2009 | Demou |
| 2009/0305337 | A1 | 12/2009 | Iqbal et al. |
| 2015/0104826 | A1 | 4/2015 | Ritterbush et al. |
| 2016/0178489 | A1 | 6/2016 | Iqbal et al. |

OTHER PUBLICATIONS

Notification of the First Office Action issued Mar. 1, 2022, from
Chinese Application No. 201980053731.3, 7 sheets.

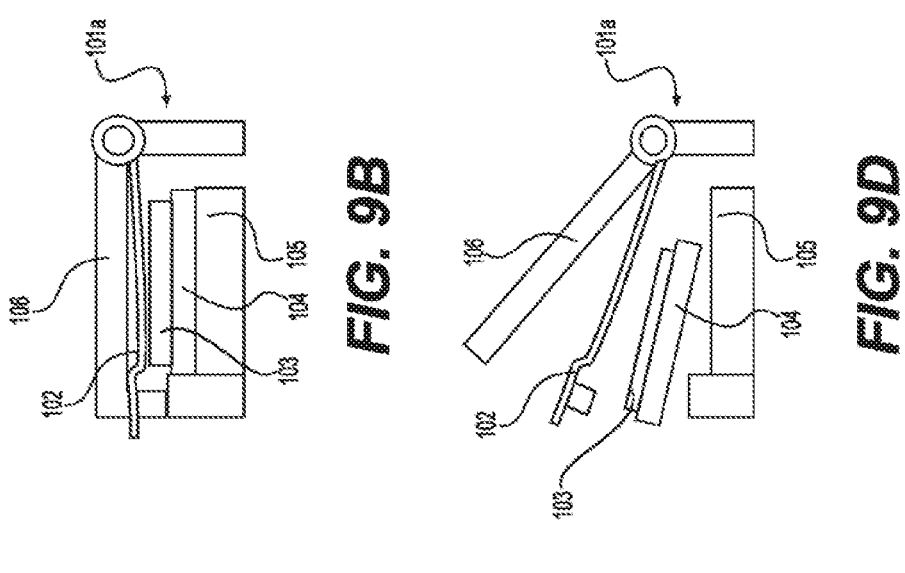
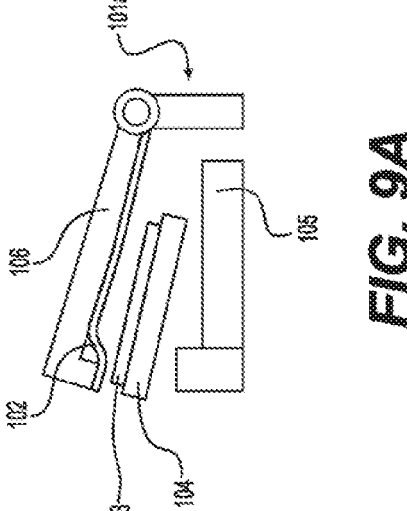
*FIG. 9A*
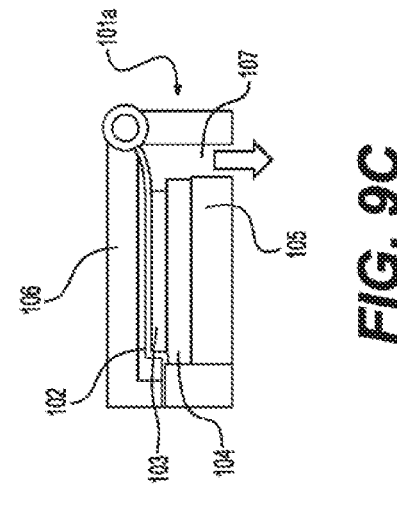
*FIG. 9C*

| Type of cancer | List of gene mutations |
| --- | --- |
| Breast cancer | ATM, BARD1, BRCA1, BRCA2, CDH1, CHEK2, NBN, MSH6, NF1 PALB2, PMS2, PTEN, STK11, TP53 |
| Ovarian/fallopian tube cancer | BRCA1, BRCA2, BRIP1, RAD51C, RAD51D, EPCAM, MLH1, MSH2, MSH6, PMS2, STK11 |
| Pancreatic cancer | BRCA1, BRCA2, EPCAM, MLH1, MSH2, MSH6, PMS2, TP53, STK11 (ATM and PALB2 require further study) |
| Prostate cancer | BRCA1, BRCA2, CHEK2, (ATM and NBNrequire further study) |
| Melanoma | BRCA1, BRCA2, PTEN |
| Uterine cancer | EPCAM, MLH1, MSH2, MSH6, PMS2, PTEN, STK11 |
| Colon cancer | CHEK2, EPCAM, MLH1, MSH2, MSH6, PMS2, PTEN, STK11, TP53 |
| Gastric cancer | CDH1, STK11 |

FIG. 11

DEVICES AND CARTRIDGES FOR EXTRACTING BIO-SAMPLE REGIONS AND MOLECULES OF INTEREST

CROSS REFERENCE TO RELATED APPLICATIONS

This application is a 371 of PCT/US2019/45433, which has an international filing date of Aug. 7, 2019, which application claims priority of U.S. Provisional Application Ser. No. 62/715,541, entitled "DEVICES AND CARTRIDGES FOR EXTRACTING BIO-SAMPLE REGIONS AND MOLECULES OF INTEREST," filed on Aug. 7, 2018, and herein incorporated by reference in its entirety.

FIELD

The present disclosure is related to methods of extracting regions and molecules of interest from biological samples, particularly through use of an automated process utilizing specifically designed bio-cartridges.

BACKGROUND

A variety of techniques have been used to extract specific biological targets from biological samples obtained from patients or subjects of medical and scientific research. Traditionally, such techniques have required often difficult (and crude) manual dissection of tissue using razors, needles or other manipulation devices to obtain quantities of individual cells identified according to their visible, histological characteristics.

A key emerging challenge in effectively diagnosing patients and treating them is applying protein, nucleotide, drug and other diagnostic and/or molecular screens to sufficient amounts of purified biological material from patient samples. For example, in order to genetically screen a cancer patient for type of cancer or for effective anti-cancer drugs or therapy, the practitioner must have enough cancer cells so that he or she can run a genetic or drug screen against those cells without being confounded by material from surrounding non-cancerous cells. In a patient sample, only a small fraction of tissue and cells may be cancerous, and those cells may occupy a complex shape in the tissue or biological sample. In order to collect enough genetic material from cancer cells, instead of from surrounding non-cancerous cells, and in order to have a good signal-to-noise ratio (more genetic material from cancerous cells than genetic material from non-cancerous cells), it is advantageous to purify disease materials from patient samples, and that purification must be integrated with subsequent patient analysis, diagnosis, follow up, and treatment.

U.S. patent application Ser. No. 14/341,523 discloses methods, devices, and systems for integrating extraction and purification of bio-sample regions and materials with patient analysis, diagnosis, follow up, and treatment. The invention provides a means to insert disclosed substrates, cartridges, and cartridge-processing instrument or instruments into a standard clinic or pathology labora-tory workflow. Specifically, the invention discloses methods, devices, and systems for inserting standard pathology slides into disclosed cartridges and cartridge-processing instruments, either manually, semi-automatically, automatically, or by robotic means. The methods, devices, and systems disclosed in U.S. patent application Ser. No. 14/341,523 are incorporated herein.

U.S. Pat. No. 8,597,715 discloses a method of removing a target from a biological sample which involves placing a transfer surface in contact with the biological sample, and then focally altering the transfer surface to allow selective separation of the target from the biological sample. The target is a cell or cellular component of a tissue section and the transfer surface is a film that can be focally altered to adhere the target to the transfer surface. Subsequent separation of the film from the tissue section selectively removes the adhered target from the tissue section. The transfer surface is focally altered by the target (e.g., by optically-induced heating from antibody binding of a dye or marker), and that alteration is then activated to adhere the target to the transfer surface. Such in situ alteration can be achieved by exposing the biological sample to an immunoreagent that specifically binds to the target (or a component of the target). The immunoreagent can alter the transfer surface directly (for example with a heat generating enzyme carried by the immunoreagent), or indirectly (for example by absorbing heat from optical illumination and transferring that heat to the target focally). Activation can occur for example by illuminating or heating the target to adhere it to a thermoplastic transfer surface. The immunoreagent can deposit a precipitate in the target that increases its light absorption relative to surrounding tissue, such that the biological specimen can be exposed to light to selectively heat the target. Alternatively, the immunoreagent is an immunofluorescent agent that carries a fluorophore that absorbs light and emits heat. The methods and substrates disclosed in U.S. Pat. No. 8,597,715, and its related patents, U.S. Pat. Nos. 7,695,752, and 7,709,047, are incorporated herein.

Below we disclose methods, devices, and systems for integrating extraction and purification of bio-sample regions and materials with patient analysis, diagnosis, follow up, and treatment.

SUMMARY

We disclose devices, systems, software, algorithms and methods for extracting regions and molecules of interest from biological samples. We also disclose related methods, devices, and systems for using extracted regions and molecules for better analyzing patient health, patient disease and pathology, patient follow up, and selecting most effective treatment options for patients (e.g., drugs or treatments that are found to best or better treat patients based on extracted regions and molecules from patient samples). Related analysis can include but is not limited to nucleotide screens (for the presence or absence of genetic regions), protein screens, antibody binding, drug or therapy binding (e.g., for selecting which drugs may be effective for cancer cells or other diseased cells/materials/molecules extracted from patient biological samples). We further disclose devices, systems, software, and workflows (e.g., pathology and reference lab workflows) for integrating sample extraction and the sample purification it enables (e.g., extracting cancer cells from a patient sample that contains many other types of cells) with existing and future devices, systems, and methods for patient diagnosis and treatment. For example, we disclose extraction of disease cells (e.g., cancer cells) from patient samples and integrating that extraction and purification with devices, systems, and methods found in a pathology laboratory setting, to enable improved patient diagnosis, follow up, and treatment. We further disclose design of cartridges to press transfer surfaces to biological material, e.g., to biological materials on glass slides (to biopsy slides). Methods are further disclosed to then remove the transfer materials from the cartridge, and to automatically process (e.g. dissolve, grind down) the transfer material to release biological material it contains.

These and other advantages may be provided by, for example, by a cartridge for molecular tests that include extracting one or more biological materials from a tissue. The cartridge includes a base having a receptacle inside the base, a lid placed over the receptacle, and a gasket in the base. The base includes a transparent window placed under the receptacle, and the receptacle contains a slide on which the tissue is disposed. A film is disposed on an inner surface of the lid, and the film is suitable to extract the one or more biological materials from the tissue. The gasket in the base surrounds the slide. The lid creates a sealed chamber around the gasket that encloses the slide, and vacuum suction is applied through a port of the base to press the film against the tissue on the slide.

These and other advantages may be provided by, for example, by a method for molecular tests of one or more biological materials. The method includes steps of mounting a tissue on a slide, loading the slide having the tissue in a receptacle of a cartridge that contains a film disposed on an inner surface of a lid of the cartridge, pressing the film against the tissue mounted on the slide, removing the film from the cartridge; and extracting the one or more biological materials from the tissue. The tissue includes the one or more biological materials. The film is suitable to extract the one or more biological materials from the tissue. The tissue or at least a portion of the tissue adheres to the film.

These and other advantages may be provided by, for example, by a cartridge processing system for molecular tests that include extracting one or more biological materials from a tissue. The cartridge processing system includes a sealing device, one or more cartridges, and a carousel that contains the one or more cartridges and allows each cartridge to be delivered into the sealing device. the sealing device applies vacuum suction to the cartridge placed in the sealing device. The cartridge includes a base having a receptacle inside the base, a lid placed over the receptacle, and a gasket in the base. The base includes a transparent window placed under the receptacle, and the receptacle contains a slide on which the tissue is disposed. A film is disposed on an inner surface of the lid, and the film is suitable to extract the one or more biological materials from the tissue. The gasket in the base surrounds the slide. The lid creates a sealed chamber around the gasket that encloses the slide, and vacuum suction is applied through a port of the base to press the film against the tissue on the slide.

These and other advantages may be provided by, for example, by a cartridge processing system for molecular tests that include extracting one or more biological materials from a tissue. The cartridge processing system includes a table top platform, a lid disposed on the table top platform, and one or more cartridges disposed between the table top platform and the lid. The cartridge includes a base having a receptacle inside the base, a lid placed over the receptacle, and a gasket in the base. The base includes a transparent window placed under the receptacle, and the receptacle contains a slide on which the tissue is disposed. A film is disposed on an inner surface of the lid, and the film is suitable to extract the one or more biological materials from the tissue. The gasket in the base surrounds the slide. The lid creates a sealed chamber around the gasket that encloses the slide, and vacuum suction is applied through a port of the base to press the film against the tissue on the slide.

These and other advantages may be provided by, for example, by a cartridge processing system for molecular tests that include extracting one or more biological materials from tissues. The cartridge processing system includes a table top platform, a lid disposed on the table top platform, and a film disposed on an inner surface of the lid between the lid and the table top platform. The film is suitable to extract the one or more biological materials from the tissues. One or more slides, on which tissues are disposed, are placed on the table top platform. The film covers the one or more slides.

These and other advantages may be provided by, for example, a device for analysis of gene expression in extracted biological material from a cancer patient. The device include an instrument for incorporating cancer genes from a patient into living cells so that the cancer genes are expressed, a mechanism for transfer of a biological sample comprising said living cells that express cancer genes from a patient to one or more slides or one or more cartridges, in which a biological sample has been mounted on the one or more slides, or in which the one or more cartridges have been attached to one or more slides upon which a biological sample has been mounted so that a cartridge and a slide form a single unit, an instrument for processing said one or more slides or one or more cartridges, a mechanism within the instrument for extracting biological material from the biological samples on the one or more slides or one or more cartridges, in which the mechanism may operate by manual, automatic or robotic means, a processor within the instrument which may control deposition of different extracted biological materials into one or more different individual receptacles, a mechanism within the instrument for depositing the extracted biological material in one or more different individual receptacles, a mechanism within the instrument that mechanically or pneumatically or electrically inserts the one or more different individual receptacles into an analytical device, and in which the analytical device may conduct analyses comprising comparative analysis of the properties of different extracted biological material deposited in the one or more different individual receptacles.

These and other advantages may be provided by, for example, a method for purifying and extracting biological material from a biological sample for scientific analysis. The method includes inserting one or more slides or one or more cartridges into an instrument for processing said slide or cartridges, in which a biological sample has been mounted on the one or more slides, or in which the one or more cartridges have been attached to one or more slides upon which a biological sample has been mounted so that a cartridge and a slide form a single unit, extracting biological material from the biological samples on the one or more slides or one or more cartridges, in which the extracting may operate by manual, automatic or robotic means within the instrument, aligning the placement of an individual receptacle for extracted biological material with the placement of each slide or cartridge within the instrument, depositing the extracted biological material in one or more individual receptacles, inserting the individual receptacles into a device for purifying biological material, including tissue, cells, nucleotides, or proteins, purifying the extracted biological material within the individual receptacles, transferring the purified and extracted biological material to an analytical device by mechanical, pneumatic or electrical means, in which the extracted biological material within the individual receptacles is made available for analysis by the analytical device, in which the analytical device may conduct analyses comprising cell culture analysis.

These and other advantages may be provided by, for example, a device for scientific analysis of purified and extracted biological material from a biological sample. The device includes an instrument for processing one or more slides or one or more cartridges, in which a biological sample has been mounted on the one or more slides, or in which the one or more cartridges have been attached to one or more slides upon which a biological sample has been mounted so that a cartridge and a slide form a single unit, a mechanism within the instrument for extracting biological material from the biological samples on the one or more slides or one or more cartridges, in which the mechanism may operate by manual, automatic or robotic means, a mechanism within the instrument for depositing the extracted biological material in one or more individual receptacles, a mechanism within the instrument that mechanically or pneumatically or electrically inserts the individual receptacles into a device for purifying biological material, including tissue, cells, nucleotides, or proteins, a mechanism within the device for purifying biological material that mechanically or pneumatically or electrically transfers the extracted biological material to an analytical device, in which the analytical device may conduct analyses comprising cell culture analysis.

These and other advantages may be provided by, for example, a method for purifying and extracting biological material from a biological sample for scientific analysis. The method includes inserting one or more slides or one or more cartridges into an instrument for processing said slide or cartridges, in which a biological sample has been mounted on the one or more slides, or in which the one or more cartridges have been attached to one or more slides upon which a biological sample has been mounted so that a cartridge and a slide form a single unit, extracting biological material from the biological samples on the one or more slides or one or more cartridges, in which the extracting may operate by manual, automatic or robotic means within the instrument, aligning the placement of an individual receptacle for extracted biological material with the placement of each slide or cartridge within the instrument, depositing the extracted biological material in one or more individual receptacles, inserting the individual receptacles into a device for purifying biological material, including tissue, cells, nucleotides, or proteins, purifying the extracted biological material within the individual receptacles, transferring the purified and extracted biological material to an analytical device by mechanical, pneumatic or electrical means, in which the extracted biological material within the individual receptacles is made available for analysis by the analytical device, in which the analytical device may conduct analyses comprising drug screening or genetic screening of the purified and extracted biological material. Further embodiments disclose the method, in which a single individual receptacle containing extracted biological material is processed by both the device for purifying biological material and the analytical device.

These and other advantages may be provided by, for example, a method for extracting biological material from a biological sample for genetic analysis. The method includes inserting one or more slides or one or more cartridges into an instrument for processing said slide or cartridges, in which a biological sample has been mounted on the one or more slides, or in which the one or more cartridges have been attached to one or more slides upon which a biological sample has been mounted so that a cartridge and a slide form a single unit, extracting biological material from the biological samples on the one or more slides or one or more cartridges, in which the extracting may operate by manual, automatic or robotic means within the instrument, aligning the placement of an individual receptacle for extracted biological material with the placement of each slide or cartridge within the instrument, depositing the extracted biological material in one or more individual receptacles, inserting the individual receptacles into a genetic screening device by mechanical, pneumatic or electrical means, in which the extracted biological material within the individual receptacles is made available for analysis by the genetic screening device.

These and other advantages may be provided by, for example, a device for genetic analysis of extracted biological material from a biological sample. The device includes an instrument for processing one or more slides or one or more cartridges, in which a biological sample has been mounted on the one or more slides, or in which the one or more cartridges have been attached to one or more slides upon which a biological sample has been mounted so that a cartridge and a slide form a single unit, a mechanism within the instrument for extracting biological material from the biological samples on the one or more slides or one or more cartridges, in which the mechanism may operate by manual, automatic or robotic means, a mechanism within the instrument for depositing the extracted biological material in one or more individual receptacles, a mechanism within the instrument that mechanically or pneumatically or electrically inserts the individual receptacles into a genetic screening device, in which the instrument and the genetic screening device are spatially arranged so that placement of each slide or cartridge within the instrument is aligned with the placement of an individual receptacle for extracted biological material.

These and other advantages may be provided by, for example, a method for extracting biological material from a biological sample for scientific analysis. The method includes obtaining a biological sample from a subject, mounting the biological sample on a slide, optionally, attaching the slide to a cartridge so that the slide and cartridge form a single unit, inserting the slide or cartridge into an instrument for processing one or more slides or one or more cartridges, processing the one or more slides or one or more cartridges to extract biological material from the biological samples within the instrument by manual, automatic or robotic means, depositing the extracted biological material within the instrument in a position that makes the extracted biological material available for scientific analysis, transferring the extracted biological material by manual, semi-automatic or robotic means to an analytical device, in which the analytical device performs a scientific analysis of the extracted biological material, including genetic screening or protein screening. Further embodiments disclose the method, in which the analytical device is integrated with the instrument so that the analytical device and the instrument form a single unit, the method, in which the analytical device is a separate device which interfaces with the instrument by manual, semi-automatic or robotic means, the method, in which the scientific analysis is a clinical analysis or a pathology analysis.

These and other advantages may be provided by, for example, a system for extracting biological material from a biological sample for scientific analysis. The system includes an instrument for processing one or more slides or one or more cartridges, in which a biological sample has been mounted on the one or more slides, or in which the one or more cartridges have been attached to one or more slides upon which a biological sample has been mounted so that a cartridge and a slide form a single unit, a mechanism within the instrument for extracting biological material from the biological samples on the one or more slides or one or more cartridges, in which the mechanism may operate by manual, automatic or robotic means, a mechanism within the instrument for depositing the extracted biological material in a position within the instrument that makes the extracted biological material available for scientific analysis, an analytical device that interfaces with the instrument so that the extracted biological material is transferred by manual, semi-automatic or robotic means to the analytical device, in which the analytical device performs the scientific analysis, including genetic screening or protein screening.

These and other advantages may be provided by, for example, a system for extracting biological material from a biological sample for scientific analysis. The system includes an instrument for processing one or more slides or one or more cartridges, in which a biological sample has been mounted on the one or more slides, or in which the one or more cartridges have been attached to one or more slides upon which a biological sample has been mounted so that a cartridge and a slide form a single unit, a mechanism within the instrument for extracting biological material from the biological samples on the one or more slides or one or more cartridges, in which the mechanism may operate by manual, automatic or robotic means, a mechanism within the instrument for depositing the extracted biological material in a position within the instrument that makes the extracted biological material available for scientific analysis, an analytical device that is integrated with the instrument so that the analytical device and the instrument form a single unit, in which the analytical device performs the scientific analysis, including genetic screening or protein screening.

These and other advantages may be provided by, for example, a system for extracting biological material from a biological sample for scientific analysis. The system includes an instrument for processing one or more slides or one or more cartridges, in which a biological sample has been mounted on the one or more slides, or in which the one or more cartridges have been attached to one or more slides upon which a biological sample has been mounted so that a cartridge and a slide form a single unit, a mechanism within the instrument for extracting biological material from the biological samples on the one or more slides or one or more cartridges, in which the mechanism may operate by manual, automatic or robotic means, a mechanism within the instrument for depositing the extracted biological material in a position within the instrument that makes the extracted biological material available for scientific analysis. Further embodiments disclose the system, in which the extracted biological material is made available for genetic screening, including screening of nucleotides, DNA and mRNA, the system, in which the extracted biological material is made available for protein screening, the system, in which scientific analysis is conducted within the instrument itself or by one or more separate analytical devices with which the instrument is interfaced.

These and other advantages may be provided by, for example, a slide processing system for extracting biological material from one or more biological samples. The system includes a carousel, in which said carousel contains one or more slots into which one or more slides upon which a biological sample is mounted may be placed by manual or automated or robotic means, a mechanism of rotation for the carousel, in which said one or more slides are rotated to move through an ordered series of positions on the carousel, a first position on the carousel, in which a slide has a film pressed against the biological sample mounted on the slide, and in which the film comprises a substrate suitable for extracting biological material from the biological sample, and in which the film may be imaged, a second position on the carousel, in which the film may be activated so that biological material desired for extraction from the biological sample adheres to the film, a third position on the carousel, in which the film may be removed from pressing against the biological sample by manual or automated or robotic means, a fourth position on the carousel, in which the film may be reimaged, a fifth position on the carousel, in which the film may be deposited into a receptacle for further analysis of the extracted biological material. Further embodiments disclose the slide processing system, in which an analysis of the extracted biological material comprises depositing the extracted biological material on one or more individual receptacles within the carousel, or in another instrument that is interfaced with the carousel.

These and other advantages may be provided by, for example, a cartridge processing system for extracting biological material from one or more biological samples. The system includes a carousel, in which said carousel contains one or more slots into which one or more cartridges containing biological samples may be placed, a mechanism of rotation for the carousel, in which said one or more cartridges are rotated to enter inside a device, and in which said device operates a sealing mechanism, in which the sealing mechanism may seal the device and the cartridge by mechanical, hydraulic, or electrical means, or by the imposition of a vacuum, a timing mechanism which controls the period of time for which the device and the cartridge is sealed by the sealing mechanism, in which once the period of time for which the device and the cartridge are sealed is elapsed, the cartridge will be rotated by the carousel out of the device. Further embodiments disclose the cartridge processing system, in which the mechanism of rotation may operate by manual or automated or robotic means, the cartridge processing system, cartridges are placed on or removed from the carousel by manual or automated or robotic means, the cartridge processing system, in which the cartridges may be illuminated or imaged while inserted into the slots of the carousel, the cartridge processing system, in which the cartridges are assembled prior to processing by manual, automated or robotic means by a method comprising: acquiring the biological sample, orienting the biological sample to the cartridge backing or orienting the cartridge backing to the biological sample, pressing a film pre-loaded on the cartridge against the biological sample, and then sealing the cartridge by manual, automated or robotic means, the cartridge processing system, in which the biological samples may be tissue sections, whole tissue samples, histology slide, biopsy material or samples, frozen or fixed (e.g., formalin, paraffin, or ethanol fixed) samples, cellular specimens or cellular preparation, cell smears, cytology preparations, the cartridge processing system, in which films are attached to the cartridge backing by stamping, rolling, or other types of applied pressure, by shrink sealing, or by other mechanical or chemical means, the cartridge processing system, in which the cartridges are supplied with a kit containing reagents necessary for the extraction of biological material from a biological sample by the cartridge, in which the kit may comprise optical, electro-magnetic, or heat activated molecules, chemicals, biomolecules, liquid or solid reagents, ligands, antibodies, fusion molecules, polymers, visualizing agents, proteins, DNA, mRNA, enzymes, lipids, and carbohydrates, the cartridge processing system, in which the extracted biological material may be deposited in individual receptacles positioned underneath the carousel.

These and other advantages may be provided by, for example, a cartridge processing system for extracting biological material from one or more biological samples. The system includes a table-top platform, in which said table-top platform comprises a mechanism for conveying inside a device a cartridge containing a biological sample, in which said device operates a sealing mechanism, in which the sealing mechanism may seal the device and the cartridge by mechanical, hydraulic, or electrical means, or by the imposition of a vacuum, a timing mechanism which controls the period of time for which the device and the cartridge is sealed by the sealing mechanism, in which once the period of time for which the device and the cartridge are sealed is elapsed, the cartridge will be conveyed out of the device. Further embodiments disclose the cartridge processing system, in which the timing mechanism activates an auditory or visual signal when the period of time for which the device and cartridge are sealed by the sealing mechanism ends, the cartridge processing system, in which cartridges are placed on or removed from the table-top platform by manual or automated or robotic means.

These and other advantages may be provided by, for example, a cartridge processing system for extracting biological material from one or more biological samples. The system includes a cartridge-processing instrument, in which said cartridge-processing instrument comprises a top half and a bottom half linked by a hinged mechanism, said bottom half forming a stage for placement of one or more cartridges upon which are mounted biological samples, said top half forming a lid, in which said lid may be closed over the cartridges so that the cartridges are fully enclosed by the cartridge-processing instrument, a film adhered to said bottom half, in which said film comprises a substrate suitable for extracting biological material from biological samples mounted on the cartridges, and in which said film is also adhered to said top half so that closing the lid over the one or more cartridges presses the film against the one or more biological samples, a space when the lid of the cartridge-processing instrument is open so that the cartridges may be positioned inside the instrument by manual or automated or robotic means, a sealing mechanism for the cartridge-processing instrument, in which the sealing mechanism may seal the instrument and the film pressed against the cartridges by mechanical, hydraulic, or electrical means, or by the imposition of a vacuum. Further embodiments disclose the cartridge processing system, in which the system further comprises a timing mechanism which controls the period of time for which the table-top platform is sealed by the sealing mechanism, the cartridge processing system, in which the timing mechanism activates an auditory or visual signal when the period of time for which the table-top platform is sealed by the sealing mechanism ends, the cartridge processing system, in which an analysis of the extracted biological material comprises depositing the extracted biological material on one or more individual receptacles within the table-top platform, or in another instrument that is interfaced with the table-top platform.

These and other advantages may be provided by, for example, a slide processing system for extracting biological material from one or more biological samples. The system includes a slide-processing instrument, in which said slide-processing instrument comprises a top half and a bottom half linked by a hinged mechanism, said bottom half forming a stage for placement of one or more slides upon which are mounted biological samples, said top half forming a lid, in which said lid may be closed over the slides so that the slides are fully enclosed by the slide-processing instrument, a film adhered to said bottom half, in which said film comprises a substrate suitable for extracting biological material from biological samples mounted on the slides, and in which said film is also adhered to said top half so that closing the lid over the one or more slides presses the film against the one or more biological samples, a space when the lid of the slide-processing instrument is open so that the slides may be positioned inside the instrument by manual or automated or robotic means, a sealing mechanism for the slide-processing instrument, in which the sealing mechanism may seal the instrument and the film pressed against the slides by mechanical, hydraulic, or electrical means, or by the imposition of a vacuum. Further embodiments disclose the slide processing system, in which the system further comprises a timing mechanism which controls the period of time for which the slide-processing instrument is sealed by the sealing mechanism, the slide processing system, in which the timing mechanism activates an auditory or visual signal when the period of time for which the slide-processing instrument is sealed by the sealing mechanism ends, the slide processing system, in which an analysis of the extracted biological material comprises depositing the extracted biological material on one or more individual receptacles within the table-top platform, or in another instrument that is interfaced with the table-top platform.

These and other advantages may be provided by, for example, a slide processing system for extracting biological material from one or more biological samples. The system includes a table-top platform, in which said table-top platform comprises a top half and a bottom half linked by a hinged mechanism, said bottom half forming a stage for placement of one or more slides upon which are mounted biological samples, said top half forming a lid, in which said lid may be closed over the one or more slides so that the slides are fully enclosed by the table-top platform, a film attached to the lid, in which said film comprises a substrate suitable for extracting biological material from biological samples mounted on the slides, and in which closing the lid over the one or more slides presses the film against the one or more biological samples, a sealing mechanism for the table-top platform, in which the sealing mechanism may seal the platform and the film pressed against the slides by mechanical, hydraulic, or electrical means, or by the imposition of a vacuum.

These and other advantages may be provided by, for example, a cartridge processing system for extracting biological material from one or more biological samples. The system includes a table-top platform, in which said table-top platform comprises a top half and a bottom half linked by a hinged mechanism, said bottom half forming a stage for placement of one or more cartridges containing biological samples, said top half forming a lid, in which said lid may be closed over the one or more cartridges so that the cartridges are fully enclosed by the table-top platform, a sealing mechanism for the table-top platform, in which the sealing mechanism may seal the platform and the cartridges by mechanical, hydraulic, or electrical means, or by the imposition of a vacuum.

These and other advantages may be provided by, for example, a kit for extracting biological material from a biological sample. The kit includes a slide, in which the biological sample may be mounted on the slide, a cartridge, in which the slide upon which the biological sample may be attached to the cartridge to form a single unit, a film, in which the cartridge is pre-loaded with the film, said film comprising a substrate suitable for extracting biological material from the biological sample.

These and other advantages may be provided by, for example, a method of extracting biological material from a biological sample. The method includes mounting a biological sample upon a slide, attaching the slide to a cartridge that contains a pre-loaded film, in which the film comprises a substrate suitable for extracting biological material from the biological sample, pressing the film against the biological sample mounted upon the slide, ending the pressing of the film against the biological sample mounted upon the slide, removing the film from the cartridge by using a pull tab attached to the film, extracting biological material from the biological sample that has been adhered to the film.

These and other advantages may be provided by, for example, a cartridge for extracting biological material from a biological sample. The cartridge includes a film pre-loaded on the cartridge, in which the film comprises a substrate suitable for extracting biological material from the biological sample, an adjustable link for attaching the cartridge to a slide upon which the biological sample has been mounted, in which the cartridge and slide form a single unit after attaching the cartridge to the slide, a mechanism for pressing the film against the biological sample mounted on the slide when the slide is attached to the cartridge, a mechanism for ending the pressing of the film against the biological sample mounted on the slide when the slide is attached to the cartridge, a pull tab which is attached to the film, in which the pull tab enables the film to be removed from the cartridge.

These and other advantages may also be achieved by a single use cartridge that provides a vacuum seal and includes a port that enables application of a vacuum in order to vacuum seal a film to tissue on a glass slide in the cartridge. Embodiments may also include a rolling pin than enables automated removal of the film with tissue from the cartridge and removal of cells from the film outside the cartridge.

Further aspects and advantages of the invention will appear from the following description taken together with the accompanying drawings.

BRIEF DESCRIPTION OF THE DRAWINGS

The above and other objects and advantages of the invention will be apparent upon consideration of the following detailed description, taken in conjunction with the accompanying figure, in which like reference characters refer to like parts throughout.

FIG. 9A-9D is a cross-sectional view of a preferred embodiment of a cartridge with a lid with one or more components, one of these components of the lid can be opened or removed to give easy access to the underlying film.

FIG. 11 shows a table including exemplary types of cancers and list of gene mutations for which the methods and systems of the disclosed invention can be used to conduct and improve molecular tests.

DETAILED DESCRIPTION

One mode for carrying out the invention is presented in terms of its preferred embodiment, herein depicted within FIG. 1. However, the invention is not limited to the described embodiment and a person skilled in the art will appreciate that many other embodiments of the invention are possible without deviating from the basic concept of the invention, and that any such work around will also fall under scope of this invention. It is envisioned that other styles and configurations of the present invention can be easily incorporated into the teachings of the present invention, and only one particular configuration shall be shown and described for purposes of clarity and disclosure and not by way of limitation of scope.

Headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). The terms "a" and "an" herein do not denote a limitation of quantity, but rather denote the presence of at least one of the referenced items.

Cartridge Designs

According to the invention, cartridges are designed to allow the extraction of desired regions of the biological sample in a fast and efficient manner, including in a single step. Each cartridge will ensure that a substrate contacts the tissue or biological samples, that the interaction between substrate and the biological samples alters the substrate so that it is focally targeted on the region of interest, and that the alteration is then activated so that the substrate will selectively bind to specific tissue regions, cells, and molecules of interest (e.g., cancer cells from a milieu of many other cells), and will then extract those tissue regions, cells, and molecules of interest.

Figures 1A, 1B:
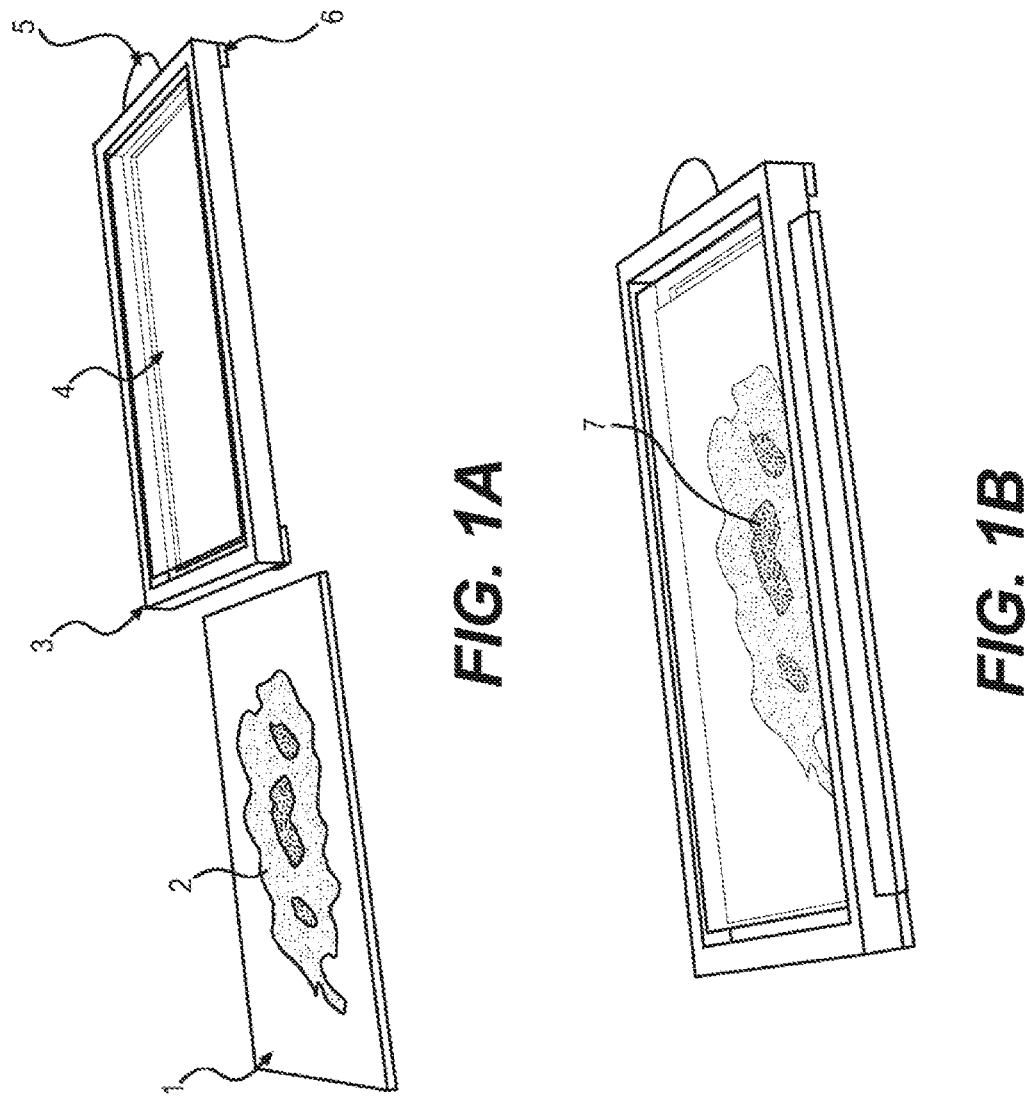
FIG. 1A is a view of a preferred embodiment, a disposable cartridge that is designed to "snap" over a microscope slide upon which a biological sample has been mounted.
FIG. 1B shows the cartridge snapped into place over the microscope slide.

Referring now to FIG. 1A, one preferred embodiment of the invention is shown in which a cartridge 3, which has been pre-loaded with a film 4 made from a suitable substrate for extracting biological material, is designed to "snap" onto a microscope slide 1 upon which a biological sample 2 has been mounted. The cartridge combines with a slide to form a single unit comprising a biological sample sandwiched between a backing that is more rigid than the sample and a sealing film that is less rigid than the sample. As shown in FIG. 1B, the cartridge is designed to fit over the microscope slide so that the film is pressed 7 against the biological sample mounted on the slide. The size of the cartridges used may vary to suit the sizes of slide available. As shown, each cartridge contains a film which is connected to a pull tab 5 which extends from one end of the cartridge sufficiently far to allow a user to grip the pull tab effectively. The actual mechanism of attaching the cartridge to the slide may be varied in accordance with methods known in the art, such as for example plastic hooks that retain sufficient flexibility to allow the slide to be held in place with the cartridge attached 6, but that will also allow the cartridge to be removed after the extraction process has been completed. The film is attached to the cartridge via means commonly known in the art.

FIG. 1B shows the cartridge and slide attached together in accordance with one preferred embodiment of the invention. The cartridge and slide pressing together combines the biological sample on the slide with the film on the cartridge, which is an optical, electro-magnetic or heat-activated substrate or contains specific molecules that allow desired target regions of the biological sample to be extracted. The film can be laid onto the tissue as the slide is inserted into the cartridge, by for example mechanically, electrically, or optically triggering a mechanism operating within the cartridge, or from outside the cartridge, that presses the film up against the tissue. Pressing can be accomplished by mechanical, hydraulic, or electrical means or preferably by the imposition of a vacuum. Alternatively, after the slide is inserted, a user can press on the cartridge or can activate a button or switch, or the cartridge may be self-activated, to initiate contact between the substrate and the tissue. After a suitable period of time, which may be determined by one of ordinary skill according to the particular kind of extraction being performed, or by a timer or other means, the cartridge is removed from the slide, at which point biological material will also be attached to the film according to the particular extraction technique used. In some embodiments, the cartridge devices of the present application are used for expression micro-dissection, a technique that allows for the procurement of desired cells or tissues via molecular targeting.

Preferably, the sealing film contains or has attached to it an optically or heat activated adherent. The cartridge device is further designed so that the biological sample region, regions, or molecules of interest may be subsequently disassociated from the sealing film. A tab, handle, groove or grooves, the material properties of the film, or a temporary or permanent attachment to the sealing film allows its easy removal from the sample by the user or the parent cartridge processing system into which the cartridge is inserted by the user. For example, the parent system or user removes the film by grasping the pull tab, by pulling the film off using small pins or guides that fit into the grooves, or by a roller that temporarily adheres to the top surface of the flexible sealing film pulling it off. When removed, the sealing film takes with it the desired region, regions or molecules of interest from the biological sample, such as in the case of expression micro-dissection. The pull tab is then pulled on by the user to remove the film from the cartridge. The sealing film may also be removed from the cartridge automatically by mechanical means as part of a larger device into which the cartridge has been inserted for processing. The film may be imaged while pressed on top of the slide, after the initial removal of the cartridge from the slide, or after the film itself is removed from the cartridge by the pull tab. After the film has been removed from the cartridge the film may be further analyzed according to the experimental goals of the user, while the cartridge itself is disposed of Cartridges in this preferred embodiment are made of disposable plastic or alternative similar materials, which are inexpensive but durable. The material from which the cartridge is made is not limiting upon the invention. The cartridge device is further designed so that the biological sample region, regions, or molecules of interest may be subsequently disassociated from the sealing film.

In preferred embodiments, the sealing film material is chosen/designed so that it can be readily dissolved, or so that its adherence can be reversed releasing the target parts of the biological sample into a chamber or test-tube which forms part of a larger cartridge-processing system. Alternatively, the biological regions or molecules can be scraped off, washed off, or removed by other means inside or outside of a cartridge-processing system.

Examples of the backing materials of the cartridge include, but are not limited to glass, silicon, polymer, polystyrene, plastic, rubber, paper, wood, metal, or alloys. Examples of the sealing film materials include, but are not limited to, polymer, polystyrene, wax, rubber, silicon, silicone, paper, cloth, metal, alloys, an impregnated web, or a liquid material that dries or otherwise hardens to form a flexible, semi-flexible, or rigid covering.

The invention does not depend on a particular embodiment of the cartridge design. For example, in one embodiment the cartridge may be attached on only on one side of the slide, or in another embodiment the cartridge may be designed to contact the slide at all corners of the slide or only on some edges (for example, a C shape that fits around three edges of a slide). The cartridge device may comprise rigid, semi-rigid or flexible layers. The cartridge can be shaped in a specific way so that it correctly orients inside a particular cartridge-processing system, including if need be to align with illumination and biological sample removal mechanisms. The biological sample could be oriented facing up or down, on flexible, semi-flexible, or rigid portions of the cartridge device. The cartridge device could have just a minimal number of layers, or it could be advantageous to include more layers to ease, improve, or speed-up removal and subsequent processing of targets from the biological sample.

Figures 2A, 2B:
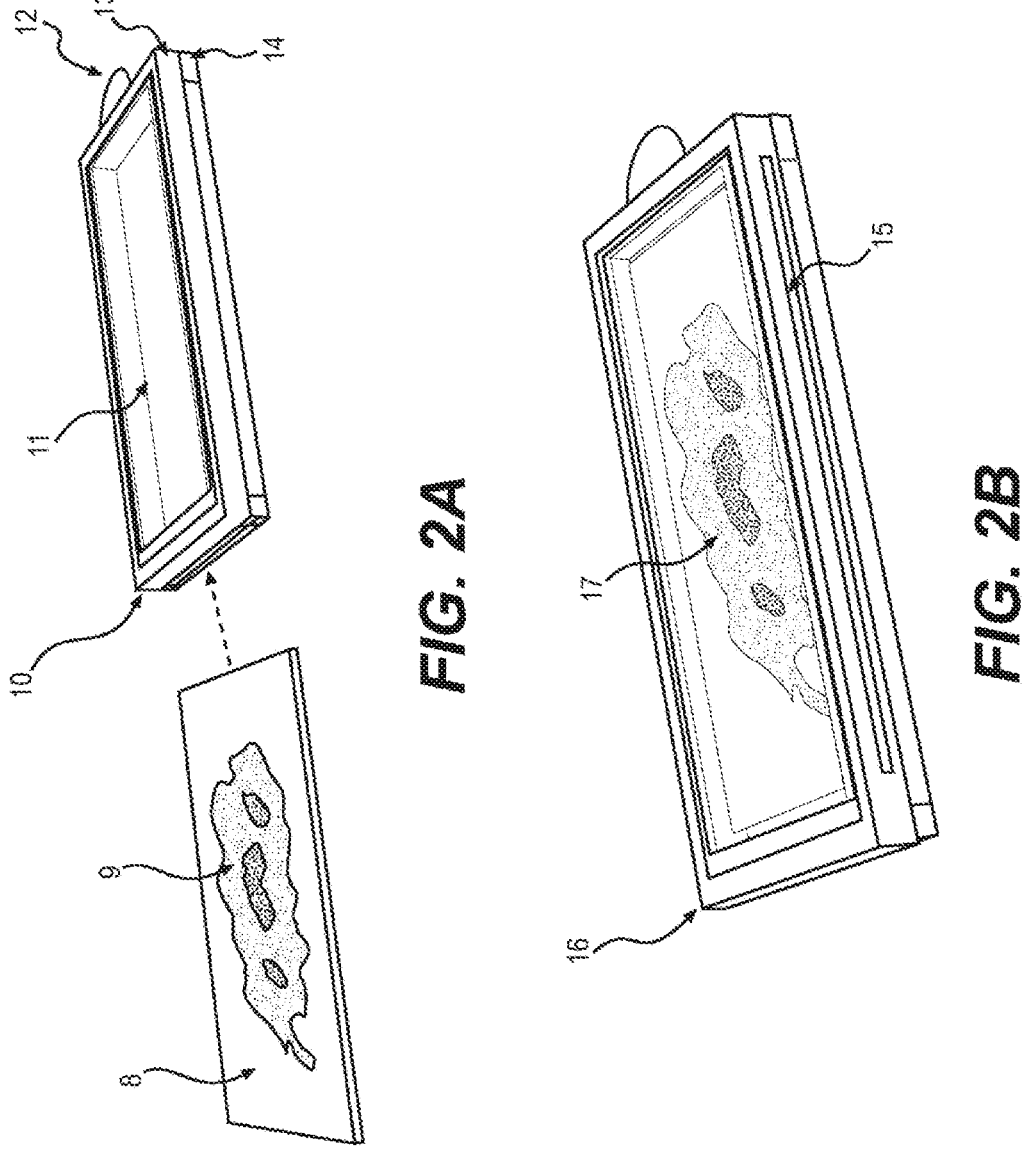
FIG. 2A is a view of another preferred embodiment, a reusable cartridge that is designed to receive a microscope slide upon which a biological sample has been mounted.
FIG. 2B shows the cartridge with the slide inserted and contained within the cartridge.

Referring now to FIG. 2A, one preferred embodiment of the invention is shown in which a cartridge device 10 is designed so that it will fully enclose a microscope slide 8 upon which a biological sample 9 has been mounted. As shown in the figure, the cartridge is designed so that the microscope slide will fit into the bottom half 14 of the cartridge device. The size of the cartridges used may vary to suit the sizes of slide available. As shown, the top half 13 of each cartridge contains a film 11 which is connected to a pull tab 12 which extends from one end of the cartridge sufficiently far to allow a user to grip the pull tab effectively. The means by which the top half and bottom half of the cartridge interact may be varied according to means commonly known in the art. The actual mechanism of attaching the top half of the cartridge to the bottom half of the cartridge is not limiting on the invention. For example, the cartridge may be hinged at on end so that the top half of the cartridge may be snapped upward from its position over the slide, or the cartridge may be designed so that the top half of the slide may be detached entirely from the bottom half of the slide. The slide is contained securely within the bottom half of the cartridge regardless of the manner in which the top half of the cartridge interacts with the bottom half of the cartridge. The film is attached to the top half of the cartridge via means commonly known in the art.

FIG. 2B shows the cartridge and slide attached together in accordance with one preferred embodiment of the invention. In this preferred embodiment, the slide 15 is contained completely within the cartridge 16 so that it is inaccessible from the surrounding environment. The cartridge and slide pressing together combines the biological sample 17 on the slide with the film on the cartridge, which is an optical, electro-magnetic or heat-activated substrate or contains specific molecules that allow desired target regions of the biological sample to be extracted. The film can be laid onto the sample after the slide is inserted into the bottom half of the cartridge by, for example, mechanically, electrically, or optically triggering a mechanism within the cartridge that presses the film up against the tissue. Pressing can be accomplished by mechanical, hydraulic, or electrical means or preferably by the imposition of a vacuum. Alternatively, after the slide is inserted, a user can press on the cartridge or can activate a button or switch, or the cartridge may be self-activated, to initiate contact between the substrate and the tissue.

Figure 2C:
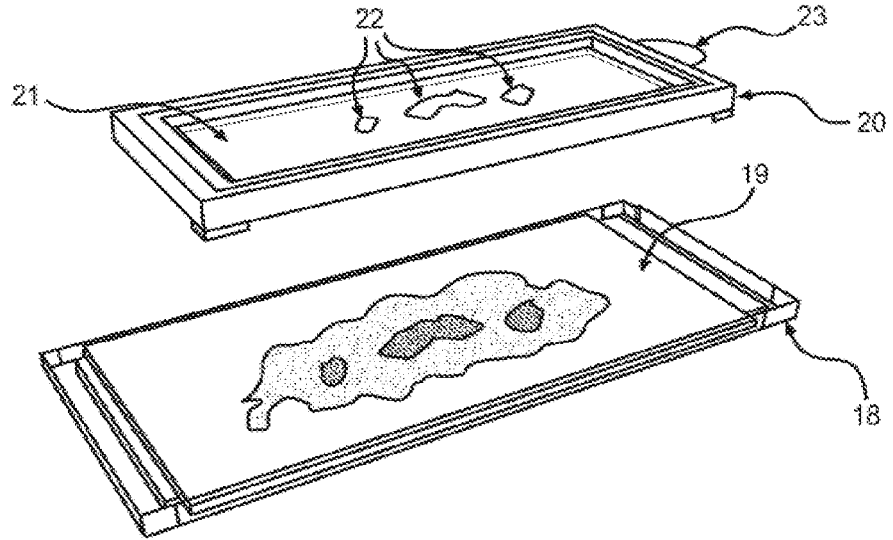
FIG. 2C shows the cartridge opened up after extraction of biological material from the sample on the slide has occurred.

FIG. 2C shows the bottom half of the cartridge 18 and slide 19 after the extraction has been completed and the top half 20 of the cartridge has been raised or detached from the bottom half of the cartridge so that the film 21 may be removed in accordance with one preferred embodiment of the invention. After a suitable period of time, which may be determined by one of ordinary skill according to the particular kind of extraction being performed, the top half of the cartridge is raised from the slide, at which point biological material 22 will also be attached to the film according to the particular extraction technique used. The pull tab 23 is then pulled on by the user to remove the film from the top half of the cartridge.

Figure 2D:
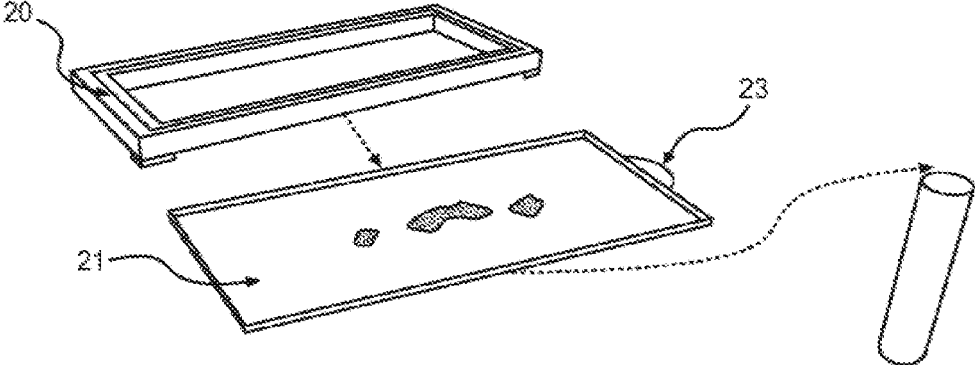
FIG. 2D shows the film on which extracted biological material is adhered removed from the top half of the cartridge.

The film may be imaged while pressed on top of the slide or after the film itself is removed from the cartridge by the pull tab. FIG. 2D illustrates the film 21 removed from the top half 20 of the cartridge by means of the pull tab 23. The film may then be placed in a test tube, vial or other suitable receptacle as shown. After the film has been removed from the top half of the cartridge the film may be further analyzed according to the experimental goals of the user, while the cartridge itself may be re-used or disposed. Cartridges in this preferred embodiment may be made of re-usable plastic or alternative similar materials, which are both inexpensive but durable. The material from which the cartridge is made is not limiting upon the invention.

Embodiments provide means to insert disclosed substrates, cartridges, and cartridge-processing instrument or instruments into a standard clinic or pathology laboratory workflow. Specifically, we disclose methods, devices, and systems for inserting standard pathology slides into disclosed cartridges and cartridge-processing instruments, either manually, semi-automatically, automatically, or by robotic means. We further disclose methods, devices, and systems for providing substrates with their attached materials (extracted and purified tissue, cells, molecules, proteins, nucleotides) to systems and instruments to carry out genetic screening, protein screening, drug or therapy screening, as well as to systems and methods that will suggest patient diagnosis (e.g., by genetic screening, or by automated computer-vision or imaging and software processing to assess morphology and diagnose disease), will suggest and track patient follow up, and will suggest or select patient treatment. The subsequent screening and diagnosis steps could be carried out by instruments linked to our disclosed slide and cartridge-processing instruments, for example by having the slide and cartridge-processing instrument provide purified materials to a downstream DNA analysis instrument. Alternatively, the two systems could be combined into one instrument that achieves both or more tasks.

These and other advantages may be provided by, for example, a method of analysis of extracted biological material from a subject. The method may take or obtain one or more biological samples from a subject, transfer a biological sample to one or more slides or one or more cartridges, in which a biological sample has been mounted on the one or more slides or the one or more cartridges have been attached to one or more slides upon which a biological sample has been mounted so that a cartridge and a slide form a single unit, insert said one or more slides or one or more cartridges into an instrument for processing said one or more slides or one or more cartridges, extract biological material from the biological samples on the one or more slides or one or more cartridges, deposit extracted biological materials from one or more biological samples into individual receptacles, insert the individual receptacles into a device for purifying biological material, including tissue, cells, nucleotides, or proteins, in which the instrument and the device for purifying biological material are integrated as a single unit or exist as separate units which are interfaced, and transfer purified and extracted biological material to an analytical device, in which the analytical device may conduct analyses comprising genetic or protein analysis.

Cartridge Processing Systems

Figures 3A, 3B:
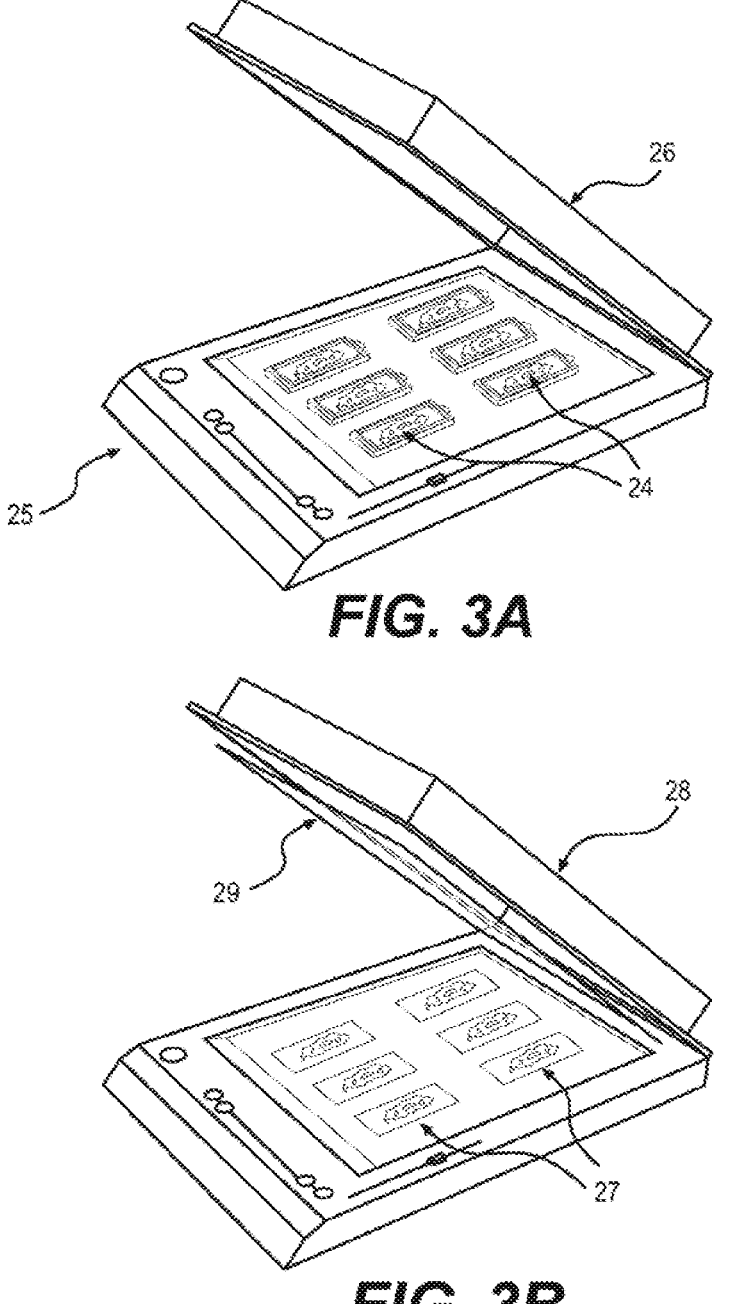
FIG. 3A is a view of a preferred embodiment, which is a manually operated table-top cartridge processing system designed to enable a user to operate a vacuum seal over cartridges when the lid of the cartridge processing platform is closed.
FIG. 3B shows an alternative embodiment of the invention, in which slides with biological samples mounted on them are placed in parallel on a table-top platform designed to bring a substrate into contact with the samples when the lid is closed.

The cartridge processing system can function "in parallel" or "in series" so that one or many slides with patient tissue may be deposited into one parent device. Referring now to FIG. 3A, one preferred embodiment is shown in which cartridges are processed by an "in parallel" cartridge processing system which is designed to be operated manually. Such "in parallel" cartridge processing systems may be designed as table-top platforms that may be square, rectangular or any other suitable shape. As shown, the system is designed to allow the placement of manually assembled cartridges 24 containing biological samples into a "waffle iron-style" table-top platform 25 designed for that purpose. The platform is then equipped with a hinged lid 26 which is sealed over the cartridges and a vacuum is applied to seal the cartridges by standard means known in the art. The cartridge processing system may be equipped with a timer to control the period for which a vacuum is applied. The user may be alerted to the completion of the vacuum sealing process either through a light or sound emitted by the platform. The hinged lid may then be opened by the user and the cartridges manually extracted and the film removed for further processing/analysis as desired by the user. The hinged lid may be designed to contain, for example, a light or heat source, which can be used to activate adhesion of biological material for extraction to the film contained in each of the cartridges.

In such embodiments, one or many slides with patient tissue could be deposited into a "waffle iron-style" table-top platform, for example, by being laid tissue up or tissue down into receptacles arranged in a preferentially planar configuration in the cartridge-processing system. The slides could be deposited manually, or automatically by a slots and guides, by rollers, by motors, by other mechanical means, by pneumatic means, or by robotic placement. The invention is not limited by the particular manner in which cartridges are placed in the cartridge processing system, or whether the process is manual or automated.

FIG. 3B shows an alternative embodiment of the "in parallel" cartridge processing system that includes table top platform 25 equipped with a lid 28 which is sealed over the slides 27. A vacuum suction may be applied to seal the slides by standard means known in the art. When the lid 28 of the cartridge-processing system is closed over on top of the slides 27 with tissue, a substrate film 29 that is big enough to cover all the slides will be brought into contact with the tissue of the slides. The contact can be improved by pneumatic means (e.g., by air suction) or by mechanical means (pads that press the substrate down onto the tissue of the slides) when the lid is closed. It is understood that the means of ensuring adequate contact between the substrate and the biological tissue for all the samples can be designed per slide or cartridge (e.g., many individual presses, one each above each tissue sample or cartridge) or can be configured to act on all slides or cartridges at once (e.g., one large press that is big enough to cover all slides or cartridges in the planar cartridge-processing instrument). It is also understood that whether slides or cartridges are processed is not limiting on the invention and that all devices disclosed herein may be designed to work with slides or cartridges.

The substrate may also be in the form of, or be part, of a bag. The bottom of the bag may be adhered to the bottom of, for example, a slide-processing instrument while the top of the bag is adhered to the lid of the slide-processing instrument. When the lid is open, the bag is also open, so that the slides or cartridges may be positioned inside the slide-processing instrument, by manual or automated or robotic means. Once the instrument is closed, the bag will be sealed and then can be vacuumed out (air removed) or pressed on by mechanical means to ensure adequate contact between the substrate and all the slides or open cartridges.

In another embodiment, the cartridge-processing instrument can be configured so that there are many substrate bags, including one bag per slide or cartridge or one bag per few slides or cartridges. It is understood that the bag does not have to be made wholly out of substrate material, but only the part of the bag that will come in contact with tissue or biological samples should be made out of the substrate that can bind to tissue regions or molecules of interest.

It is understood that the "in-parallel" cartridge-processing instrument above can be configured in many different configurations, for example the cartridges or slides or other biological samples may be placed horizontally or vertically or at angle, the substrate may be above or below the slides or cartridges, and there are other modifications that will be obvious to someone knowledgeable in the art. This instrument will "in parallel" carry out the steps of laying the substrate up against the tissue on the slide or in or on a cartridge. The substrate would be altered by interaction with the biological sample and then activated by, for example, illumination so that the target region of interest adheres to the substrate. After activation, the substrate would be pulled off with extracted/desired tissue, cells, and molecules on the substrate (for example by opening the lid of the instrument and peeling back the substrate from the tissue or biological samples). After extraction, the substrate could be deposited into receptacles, each single receptacle associated with a single slide or cartridge and then processed (extracted materials released, or substrate dissolved) to deposit the desired selected and purified materials from the patient samples into individual receptacles, for subsequent analysis either in the "in parallel" cartridge-processing instrument or in a subsequent instrument. If in a subsequent instrument (e.g., a DNA screening instrument), the transfer of purified materials from the slide or cartridge-processing instrument could be achieved by mechanical or pneumatic or robotic means. In particular, the cartridge-processing and subsequent instrument could have matching interfaces (same location of slots for samples) so that transfer of materials from one to the other would be simple, reliable, fast, and convenient.

Figure 4:
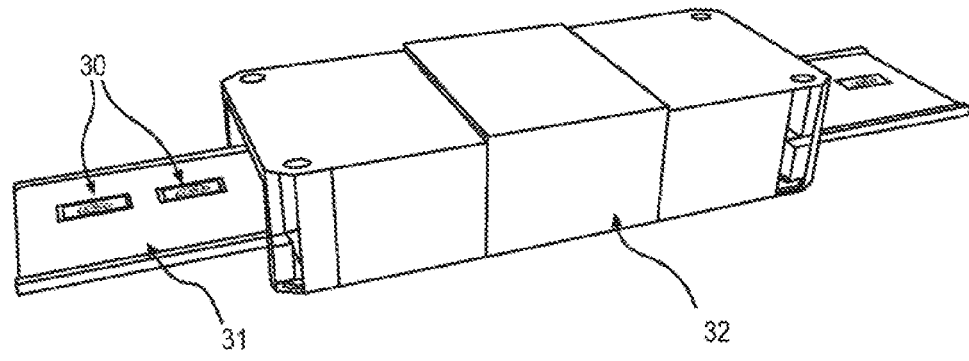
FIG. 4 is a view of a preferred embodiment, which is an "in series" cartridge processing system, which is designed to operate semi-automatically.

Referring now to FIG. 4, one preferred embodiment is shown in which cartridges are processed by an "in series" cartridge processing system, which is designed to operate semi-automatically. Cartridges containing biological samples 30 may be manually assembled and then placed on a platform (such as a conveyor belt 31) designed to convey cartridges in series into a vacuum sealing device 32. After the vacuum sealing process has been applied, the cartridge processing system is then designed to convey the cartridge out of the vacuum sealing device, after which the film may be extracted for further processing/analysis as desired by the user. The invention is not limited by the design of the "in series" conveyance system, the method of sealing the film or whether the device is primarily manually operated or automatically operated.

Figure 5:
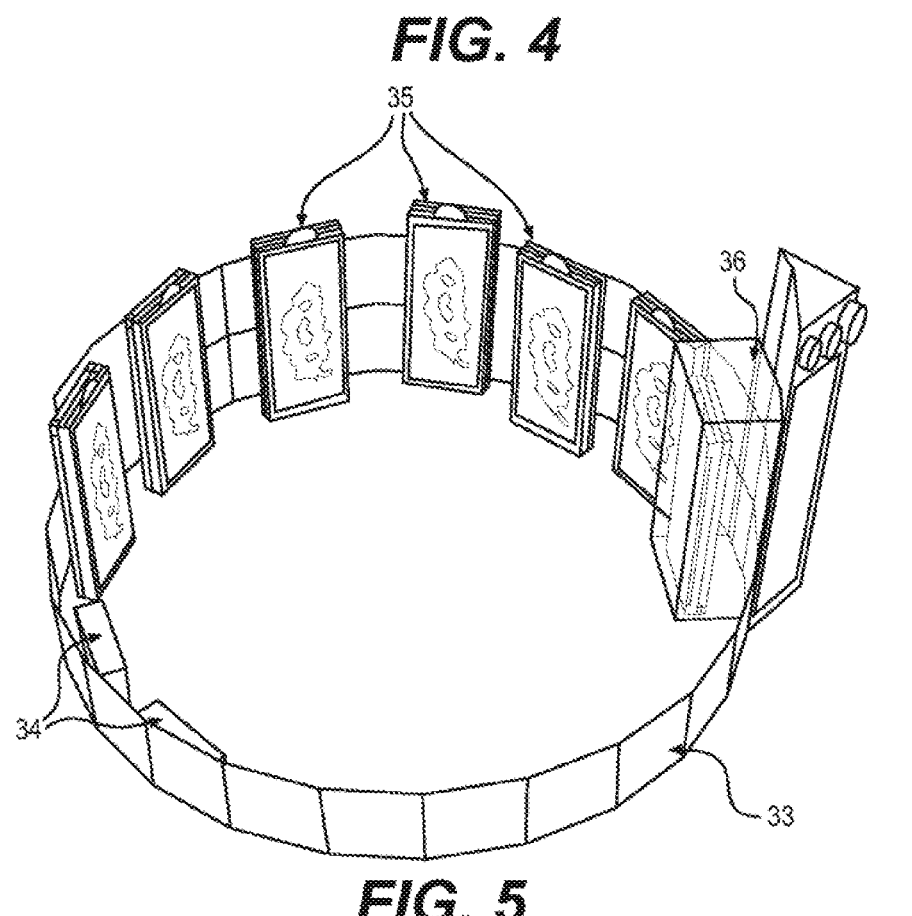
FIG. 5 is a view of a preferred embodiment, which is a cartridge-processing system may be designed as a carousel where cartridges with tissue are entered into slots, and rotation of the carousel causes each cartridge to be processed.

Referring now to FIG. 5, in one preferred embodiment of the invention a cartridge-processing system may be designed as a carousel 33 where slides or cartridges 35 with tissue are entered into slots 34, and rotation of the carousel causes each cartridge to be processed. Cartridges containing biological samples may be manually assembled and then placed on a carousel designed to convey cartridges in series into a vacuum sealing device 36 or to a device with a different sealing mechanism (e.g., mechanical pressing force to seal triggered by mechanisms within or outside the cartridge/ slide). After the vacuum sealing process has been applied, the cartridge processing system is then designed to convey the cartridge out of the sealing device, after which the film may be extracted for further processing/analysis as desired by the user. The invention is not limited by the design of the carousel, the method of sealing the film or whether the device is primarily manually operated or automatically operated.

In some embodiments, the slides or cartridge can be inserted into a cartridge-processing system that illuminates and images the cartridge. Such a cartridge processing system may be designed to efficiently and automatically process one or more cartridges while recording such images.

Figure 6:
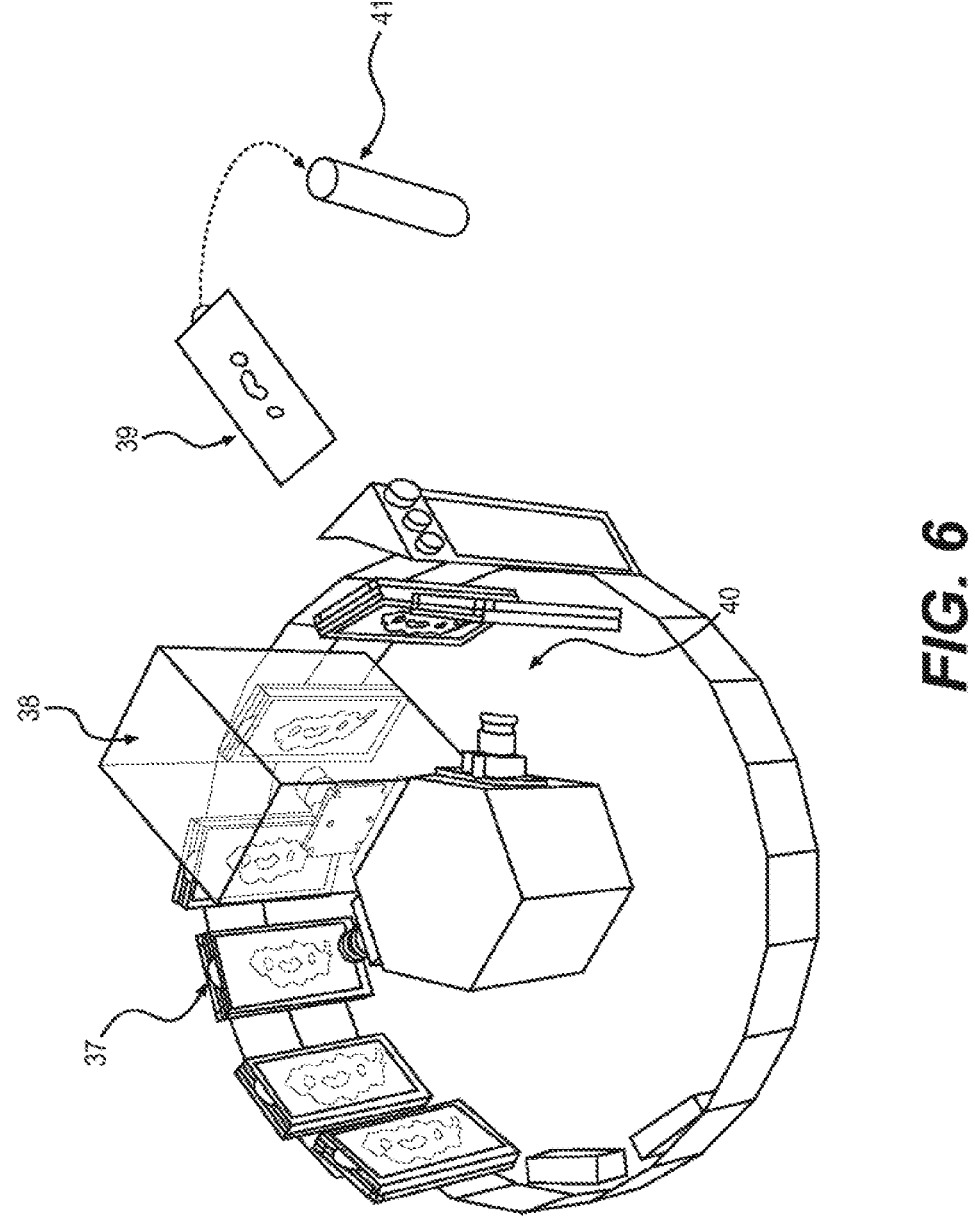
FIG. 6 is a view of a preferred embodiment, which is a cartridge assembly system to creates and processes the cartridge devices through an automated process.

Referring now to FIG. 6, in another embodiment of the invention the slides or cartridge can be inserted into a parent cartridge-processing system that illuminates and images the cartridge, and the cartridge design allows the extraction of desired regions of the biological sample in a fast and efficient manner, including in a single step. Such a parent instrument will efficiently and automatically process one or more cartridges. It will ensure that the substrate contacts the tissue or biological samples, will activate the substrate to selectively bind to specific tissue regions, cells, and molecules of interest (e.g., cancer cells from a milieu of many other cells), and will then extract those tissue regions, cells, and molecules of interest. The parent cartridge-processing system could be designed as a carousel where slides with tissue are entered into slots, and rotation of the carousel causes each slide to be processed.

For instance, in a first location 37 the substrate could be laid up against the tissue on the slide and imaged, in a second location 38 the substrate could be activated, in a third location 39 the substrate could be pulled off with extracted/desired tissue, cells, and molecules on the substrate, in a fourth location 40 the slide could be reimaged, and in a fifth location 41 the substrate could be deposited in a receptacle and processed (extracted materials released, or substrate dissolved) to deposit the desired selected and purified materials from the patient samples into the receptacle. Slides with tissue samples, or other bio samples, would be moved from one location to the next, thus ensuring that many patient slides are processed in sequence by the carousel cartridge-processing system. The extracted and purified materials for each sample could then be analyzed (DNA screens, protein analysis, drug or therapy screens or binding analysis) in the parent cartridge-processing system, or could be manually or automatically provided by a downstream instrument or system.

The transfer of purified materials from the slide or cartridge-processing instrument to another subsequent analytical instrument can be achieved by mechanical or pneumatic or robotic means. In particular, the cartridge-processing and any subsequent instrument may have matching interfaces (same location of slots for samples) so that transfer of materials from one to the other would be simple, reliable, fast, and convenient.

These and other advantages of the disclosed invention may be provided by, for example, an automated system for analysis of extracted biological material from a subject. The system includes an instrument for taking one or more biological samples from a subject by automated means, a mechanism within the instrument for transfer of a biological sample to one or more slides or one or more cartridges, in which a biological sample has been mounted on the one or more slides or the one or more cartridges have been attached to one or more slides upon which a biological sample has been mounted so that a cartridge and a slide form a single unit, an mechanism within the instrument for processing said one or more slides or one or more cartridges, a mechanism within the instrument for extracting biological material from the biological samples on the one or more slides or one or more cartridges, a processor within the instrument which may control deposition of extracted biological materials from one or more biological samples into individual receptacles, a mechanism within the instrument for depositing extracted biological materials from one or more biological samples into individual receptacles, and a mechanism within the instrument that mechanically or pneumatically or electrically inserts the individual receptacles into a device for purifying biological material, including tissue, cells, nucleotides, or proteins. The system for purifying biological material may be integrated as a single unit or exist as separate units which are interfaced by automatic means and the system may also include a mechanism for purifying biological material that mechanically or pneumatically or electrically transfers the extracted biological material to an analytical device, in which the analytical device may conduct analyses comprising genetic or protein analysis.

Cartridge Assembly Systems

We also disclose a cartridge assembly system to create the cartridge devices. This assembly system could be part of the cartridge-processing system that will process the cartridge device, or it could be a separate system. In the cartridge assembly system, biological samples, such as tissue sections, whole tissue samples, histology slide, biopsy material or samples, frozen or fixed (e.g., formalin, paraffin, or ethanol fixed) samples, cellular specimens or cellular preparation, cell smears, cytology preparations, and biofilms are attached to the cartridge backing by stamping, rolling, or other types of applied pressure, by shrink sealing, or by other mechanical or chemical means. The assembly system takes in the biological sample, orients it to the cartridge backing or orients the cartridge backing to the biological sample, and then creates and seals the cartridge by the above mentioned means.

The cartridge could also be combined with necessary reagents provided in a kit supplied to the user. For example, the cartridge assembly system could take in a biological sample, cartridge materials (e.g., backings, films, etc.), and any necessary reagents provided in the kit (e.g., optical, electro-magnetic, or heat activated molecules, chemicals, biomolecules, liquid or solid reagents, ligands, antibodies, fusion molecules, polymers, visualizing agents, proteins, DNA, mRNA, enzymes, lipids, carbohydrates, etc.), and process them to make the assembled cartridge device. Together, the cartridge materials and the reagents in the kit would provide all the necessary materials to carry out extraction of the desired region, regions, or molecules from the biological samples.

Post-Cartridge Processing Analysis

Slides or cartridges are processed by either an "in-series" or "in-parallel" cartridge-processing instrument, which will extract and purify genes (DNA, mRNA, etc.), proteins, cancer cells, or other materials/molecules from patient samples on a per sample basis. After this process, to integrate tissue, cell, and molecule extraction and purification with genetic and protein screens, the purified materials will be screened for nucleotides or proteins using methods known in the art.

For instance, after processing in the cartridge-processing instrument, purified samples would be deposited automatically or robotically into vials or test tubes, with purified materials from each sample being deposited into a separate vial or test tube. In a carousel "in-series" configuration, vials or test tubes could be underneath the carousel and once each sample has been extracted and purified, it would be deposited into a vial or test tube.

Similarly, in an "in-parallel" slide or cartridge processing instrument, slides or vials or other receptacles would, for example, be placed underneath each slide or cartridge, and purified materials would be deposited into them. In a preferred embodiment, purified material from each slide or cartridge would be deposited into one vial or receptacle. The genetic material would then be analyzed, e.g., screened for the presence or absence of one or many specific genes or gene fragments or DNA or mRNA sequences, using currently known methods or future methods. Likewise, protein or other material could also be screened, quantified, or analyzed using known methods or future methods. Such analysis could be done within the same instrument, or could be done in a downstream instrument. If in a downstream instrument, we disclose design of the interface between the two instruments for reliable, fast, and convenient transfer of materials. For example, instruments can be designed to operate with two layers, one layer which performs the extraction and another layer that performs the analytical stages.

For example, DNA analysis could occur in an instrument placed underneath the slide or cartridge-analysis instrument, where the vials or test tubes (each filled with purified material from a single sample) would drop down or be mechanically or pneumatically or electrically lowered into the DNA screening instrument. The two instruments would have the same spatial arrangement of slides/cartridges and vials/test tubes (or other receptacles) so that transfer of materials from one to the other would be convenient, error free, simple, and fast. It is understood that other embodiments are possible, for example transfer of materials could be horizontal instead of vertical, up instead of down, at an angle, could be achieved robotically or by other means.

The invention also discloses methods for integrating biological sample purification with screening and selection of drugs or therapies for patients. As above, purified materials (e.g., tissue, cells, nucleotides, proteins, or other biological matter) would be provided to another part of the same instrument or to a subsequent instrument. Drugs or therapy would then be screened against purified materials more effectively than against unpurified materials, using known methods. For example, in each vial, test tube, or other receptacle (one receptacle per patient sample in a preferred embodiment), known or future drug selection screens could be carried out. Drug or therapy binding or activity to purified materials could be tested per receptacle.

It also may be advantageous to provide purified patient materials to live cell cultures, to test expression of nucleotides in live cells, or to carry out drug and therapy screens against living cells that have been combined with purified materials from each patient sample.

For example, cancer genes from patients may be incorporated into living cells, expressed, and then tested against drugs or other therapies. It may be advantageous to have different materials from a single patient samples deposited into multiple receptacles and live cell cultures (e.g., patient cancer genes into one vial with cells, patient immune cells into a second vial, to test if drugs can modulate a patient's immune response to better kill cells that are expressing that patient's cancer genes). Thus the invention also discloses instruments that will deposit materials from one sample into multiple different receptacles. For example, in an instrument designed with two layers, one layer for extraction and another layer for analysis, the analytical layer for each slide/cartridge may provide up to three or more different vials for depositing of the extracted biological materials for further analysis.

Conversely, the invention also discloses deposition of materials from multiple samples into one receptacle, e.g., for further material enrichment (e.g., DNA from cancer cells from 5 slides from the same patient all deposited into one vial, to provide more DNA for that patient). Computer programs and software can track which samples are where. Radio-frequency (RF) tags, colored markings, mechanical tabs, or other known or future means may also be used to mark and keep track of cartridges, vials and test tubes to provide an extra layer of tracking to know which samples are where.

These and other advantages may be provided by, for example, a method for purifying and extracting biological material from a biological sample for scientific analysis. The method inserts one or more slides or one or more cartridges into an instrument for processing said slide or cartridges, in which a biological sample has been mounted on the one or more slides or the one or more cartridges have been attached to one or more slides upon which a biological sample has been mounted so that a cartridge and a slide form a single unit, extracts biological material from the biological samples on the one or more slides or one or more cartridges, in which the extracting may operate by manual, automatic or robotic means within the instrument, aligns the placement of an individual receptacle for extracted biological material with the placement of each slide or cartridge within the instrument, deposits the extracted biological material in one or more individual receptacles, inserts the individual receptacles into a device for purifying biological material, including tissue, cells, nucleotides, or proteins, purifies the extracted biological material within the individual receptacles, transfers the purified and extracted biological material to an analytical device by mechanical, pneumatic or electrical means, in which the extracted biological material within the individual receptacles is made available for analysis by the analytical device, the analytical device may conduct analyses including image analysis, displays medical information derived from the image analysis, in which the medical information is communicated through a network connection to a computer database. Further embodiments disclose the image analysis includes displaying diagnostic and treatment information, the image analysis includes linking by a network connection to information contained in computer databases including information from morphology, genetic screens, protein screens, or bio-molecules correlated to disease, the image analysis includes accessing computer code that enables the display of medical information, in which said medical information includes diagnostic or treatment information, the image analysis includes displaying additional metrics including 1) percent cells with expressed antibody that is indicative of a type of cancer and that would bind to a substrate and be made visible, and 2) genes that are correlated with that type of cancer, the image analysis includes displaying layered information, in which said layered information includes information regarding morphology, genes, or live cell responses.

Layered Imaging

In cancer, and in other diseases, a big part of patient diagnosis is observation of the shape and colors of tissues and cells (tissue/cell morphology). The invention discloses improved morphology analysis by providing pre-extraction and post-extraction images for tissue samples, as well as overlaying nucleotide and protein and other molecular information on tissue images. In the disclosed slide and cartridge-processing instruments, a high-resolution camera or cameras and software will be provided. The camera or cameras will take high-resolution photographs of all samples at each stage. The first image could be similar to morphology (histology) images already used routinely in the clinic and in pathology labs (e.g., H&E stains or other stains or unstained). Once of-interest tissue is removed (e.g., cancer cells, or other diseases cells), photographs or images will be taken of removed and remaining tissue.

Location of removed tissue (e.g., location of the cancer) could then be accurately displayed to the clinician or pathologist overlaid on top of the original image for each patient's sample. This would provide the clinician/pathologist with additional information (e.g., exactly where the cancer is and what areas of the slide were sampled) and would aid diagnosis and subsequent selection of treatment. Further, image analysis could provide an estimation of the amount of biological material removed from the sample, and this information may allow for better decisions on the amount and/or type of downstream testing (e.g., if a large amount of tissue is sampled the software may determine that there is enough cellular material for numerous downstream tests versus when only a small amount of tissue is sampled providing only for a single test).

When additional information is collected, e.g., which cancer genes are present in that patient's cancer cells, that information could also be overlaid on top of the image, in a useful way (as transparent colors, as animated layers, as a 3-dimensional layered image, as a clickable image, or by other known or future means that will provide effective information visually). That will further improve diagnosis and treatment capabilities. Now the clinician or pathologist will be able to see which genes are present where, for example, and better diagnose and select treatment.

For example, this will allow better estimation of the extent of tumors in patients. Protein, antibody, and other information could also be overlaid on the images. Further additional information, e.g., when genes in this region where expressed in cells, this drug was able to treat those cells, could also be overlaid. The practitioner would be provided with a rich set of information useful for diagnosis and treating patients—for example, they could see which drugs will be useful for which regions of the tumor, thus selecting the combination of drugs that can treat the whole tumor or focusing drugs on the invasive elements of the patient's tumor.

A person knowledgeable in the art would recognize that there are many other embodiments, various genetic screens, various drug screens, various visual presentations, that are equivalent to the ones presented here. Integrating patient sample purification with genetic, protein, and drug analyses, and presenting that data to clinicians and pathologists, could dramatically improve patient diagnosis and treatment.

The invention further discloses automated image processing to suggest diagnoses and treatments. The shapes and colorings of cells that are associated with diseases are known to a degree. Genetic and protein profiles that are associated with disease are also beginning to become known, and will be known better in the future.

The invention discloses instruments that store, retrieve and couple images of tissue samples, as described above, with databases for morphology, genetic screens, protein screens, and other bio-molecules correlated to disease databases, and discloses software that will suggest diagnosis and treatment options to physicians.

For example, if an image of a patient's tissue samples shows a shape that is potentially correlated with cancer but the shape and coloring of the cells is not sufficient to make a diagnosis of cancer, we disclose adding additional metrics, such as: 1) percent cells with expressed antibody that is indicative of cancer and that would bind to our substrate and be made visible, and 2) genes that are correlated with that type of cancer. Presenting a clinician with morphology plus antibody plus gene evidence of cancer, automatically, would suggest a much higher likelihood of cancer and would enable software to suggest a diagnosis of cancer. Likewise, layering together information from morphology, genes, and live cell responses, for example, could also suggest therapy. If the clinician can see that invasive portions of the tumor have genes of a certain type and when those genes were expressed in cells responded well to a certain drug, that would indicate that this drug could be a viable treatment option for that patient.

Data Handling, Patient Records

The invention discloses tags (e.g., color, RF tags, mechanical tags, electrical tags, others) and software and hardware for automated sample and data management. In one embodiment, each slide or cartridge would be marked with a sample or patient specific identifier. From then on, in every step of the process, the location, status, and processing of the sample would be tracked by tags and software. Readers in the instrument and software will assign images (e.g., morphology photographs) to each sample, before and after tissue extraction. Images of extracted and left-behind tissue will be taken and associated with before images. When the purified materials are deposited into a vial, test tube or receptacle, that receptacle will be tracked in software and hardware.

Subsequent analysis (genetic screening, protein screening, drug or therapy screens, live cell culture screens) will also be tracked, again by tags on receptacles and by software, to keep track of which screens apply to which original samples. When information from gene and drug screens is overlaid back onto the original images of tissue samples, that too will be tracked by software and stored in a database. The clinician or pathologist will be able to query any part of the process—they will be able to pull up and examine any image or data at any stage.

Furthermore, in a preferred embodiment, collected data will be automatically transmitted to patient records. When a clinician reviews a patient's record, rich layered data for that patient's samples will be available. Clinicians will be able to access such data remotely from the stored database, either after or during patient sample processing. In an another embodiment, a clinician or pathologist will be able to remotely manipulate the instruments that carry out the sample purification and collect the images and data.

The invention further discloses methods to follow patients as they progress through disease and treatment. When a patient returns for a follow up visit, his or her samples will be identified with a patient identifier that is linked to that same patient. Analysis of patient samples will proceed as above, but in addition the data and images for the follow up visit will be linked with data and images from the previous visit. Original and follow-up images and data will be presented to the clinician or pathologist side-by-side, or overlaid one on top of the other, or as an animation, or by other known or future means, so that the practitioner can readily see the progression of the patient, and can assess if treatment is or is not working effectively. That will enable clinicians to better track patient outcomes and the efficacy of therapy, and will enable better selection of treatment for patients.

Practitioners will be able to access data and images remotely. Integration of software and substrates, slides, cartridges, and cartridge-processing instruments hardware with pathology laboratory workflow and with existing and emerging genetic, protein, and drug screens, will enable superior analysis, diagnosis, follow up, and treatment of patients. Software integrated with these systems will provide an improved service to clinicians and pathologists, and will enable improved patient care.

While enabling practitioners to obtain superior analysis, diagnosis, follow up, and treatment of patients, patients will also benefit by our systems. Additional software and communication tools between the practitioner and patient will also be developed to not only include information placed into electronic medical records but also to provide patients with health related information such as treatment follow-up, treatment choices and disease management protocols.

The invention further discloses linking collected data and images to existing disease and pathology databases. In one embodiment, collected morphology images and overlaid genetic markers for cancer will be cross-referenced with existing databases of cell morphology (e.g., cancer progression scoring tests) and genetic markers for cancer. Searching algorithms will provide a clinician or pathologist with links to relevant hits (similar cell morphology, shared genetic markers) in cancer databases. Thus, when a clinician or pathologist views that patients record, our disclosed systems will not only provide tissue sample morphology overlaid with genetic information and potential drug response metrics, it will also score that morphology and genetic profile against known cancer databases.

Additional Indications/Overall Use

In the above, illustrative examples have been largely provided for cancer. However, one knowledgeable in the art would recognize that the same methods are useful for other diseases and pathologies besides cancer. We disclose using the methods described above for other diseases or pathologies, including diseases or pathologies with a genetic predisposition or component.

The disclosed integrated hardware and software system will start with a patient's sample, and will, in one automated overall system, progress that sample all the way from initial mounting through purification to genetic and drug screening. It will provide the practitioner with an integrated and automated work flow, all in one lab with one set of instruments, to go from initial patient sample to final disease diagnosis and therapy screening. The results will be automatically tied to patient records, will be accessible remotely and in real time, and will allow monitoring of patient response to therapy through subsequent follow up visits.

Further Improvements

Further embodiments add pressure sealing and film peeling, maceration, digestion, and heating to cartridges described herein. Embodiments include single-use cartridges that enables both pressure sealing (front end) and film peel-off, maceration, and digestion (back end).

Figures 7A, 7B, 7C:
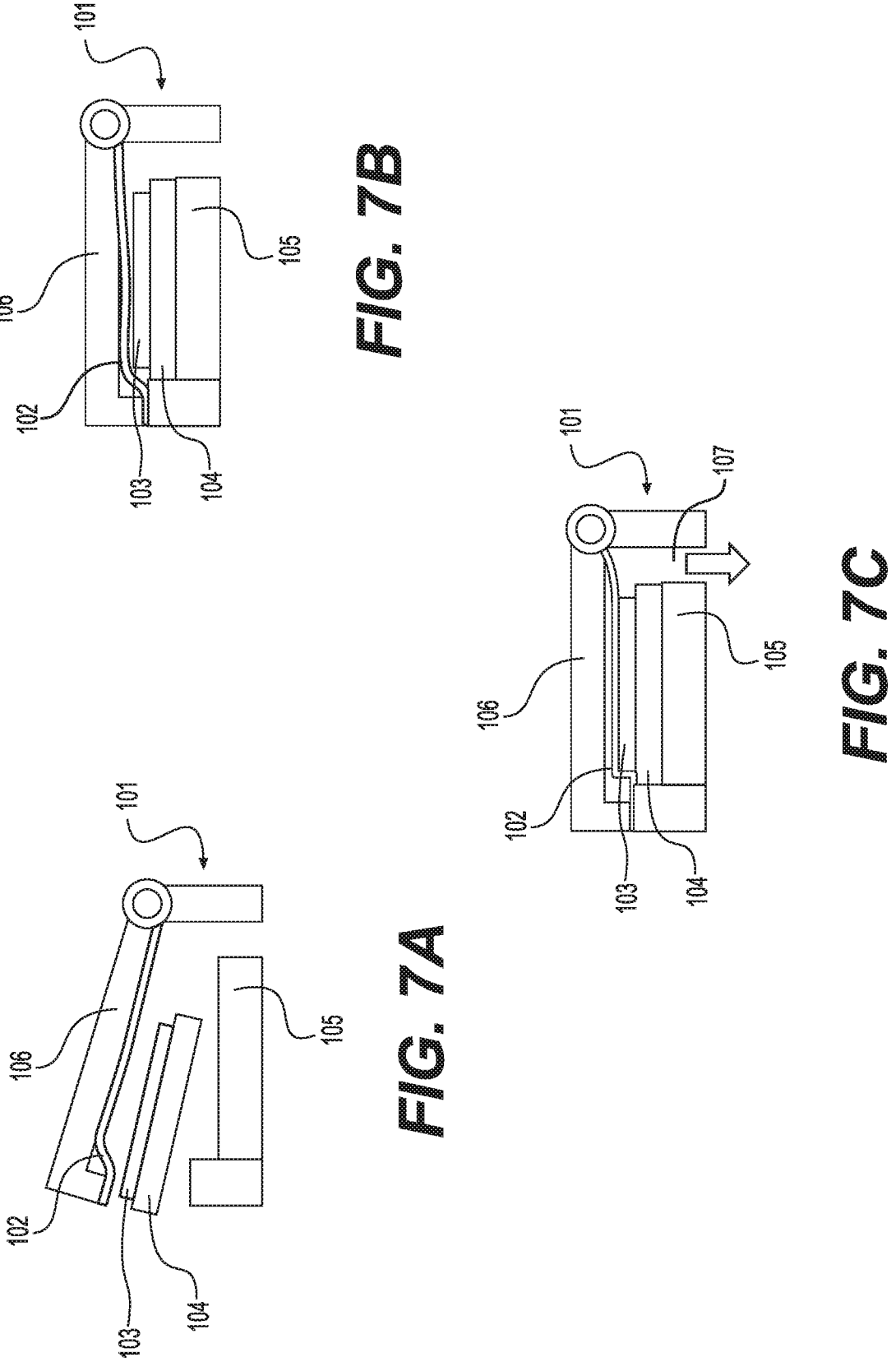
FIG. 7A-7C is a view of a preferred embodiment of cartridge capable of being vacuum-sealed.

Embodiments of the cartridges described herein allow vacuum sealing between tissue and the film. With reference now to FIGS. 7A-C, shown are an embodiment of a cartridge 101 and processes to extract biological samples from the tissue sample 103. Each such cartridge accepts a glass slide 104 (e.g., a 75 mm×26 mm glass slide commonly used to mount human biopsy samples), on which a tissue sample 103 is present. When the cartridge 101 is clamped shut, the film 102 lays onto the tissue and provides an air-tight space between the transfer film 102 and the air exit port 107. The cartridge 101 has a port 107 enabling a vacuum to be applied to the inside of the cartridge and is air-tight sealed to enable the vacuum seal to be achieved. When inserted into the instrument, e.g., a cartridge processing system, the cartridge processing system then applies a vacuum through the port 107 present in the cartridge. This vacuum presses the film 102 against the tissue 103 to ensure good thermal contact between the tissue and the film. Including film and sealing inside the cartridge allows the cartridge processing system to apply the vacuum, instead of having to rely on an external vacuum source, such as a food bag and the food sealer.

In an embodiment, as shown in FIGS. 7A-7C, each cartridge may accept one glass slide with tissue (see FIG. 7A). The cartridge 101 clamps shut to lay the film 102 on top of the tissue 103 and to provide an air-tight space between the film and the exit port 107 at the bottom right (see FIG. 7B). The cartridge processing system pulls a vacuum through the exit port 107, which presses the film 102 against the tissue (see FIG. 7C). This eliminates the need for an external sealer, such as a food bag and vacuum sealer. There is a clear (transparent) window 105 in the bottom of the cartridge 101 to allow a light to flash up into the cartridge and reach the tissue and film.

Vacuum pumps capable of applying sufficient pressure, e.g., 0.8 atmospheres of vacuum or more may be readily integrated into the cartridge processing system. Cartridges enable easy opening and closing, good vacuum sealing, and efficient transmission of flashed light to the film. Embodiments may include a bag pouch inside the cartridge that accepts the glass slide and opens and closes with the cartridge to provide the air-tight seal.

Figure 8:
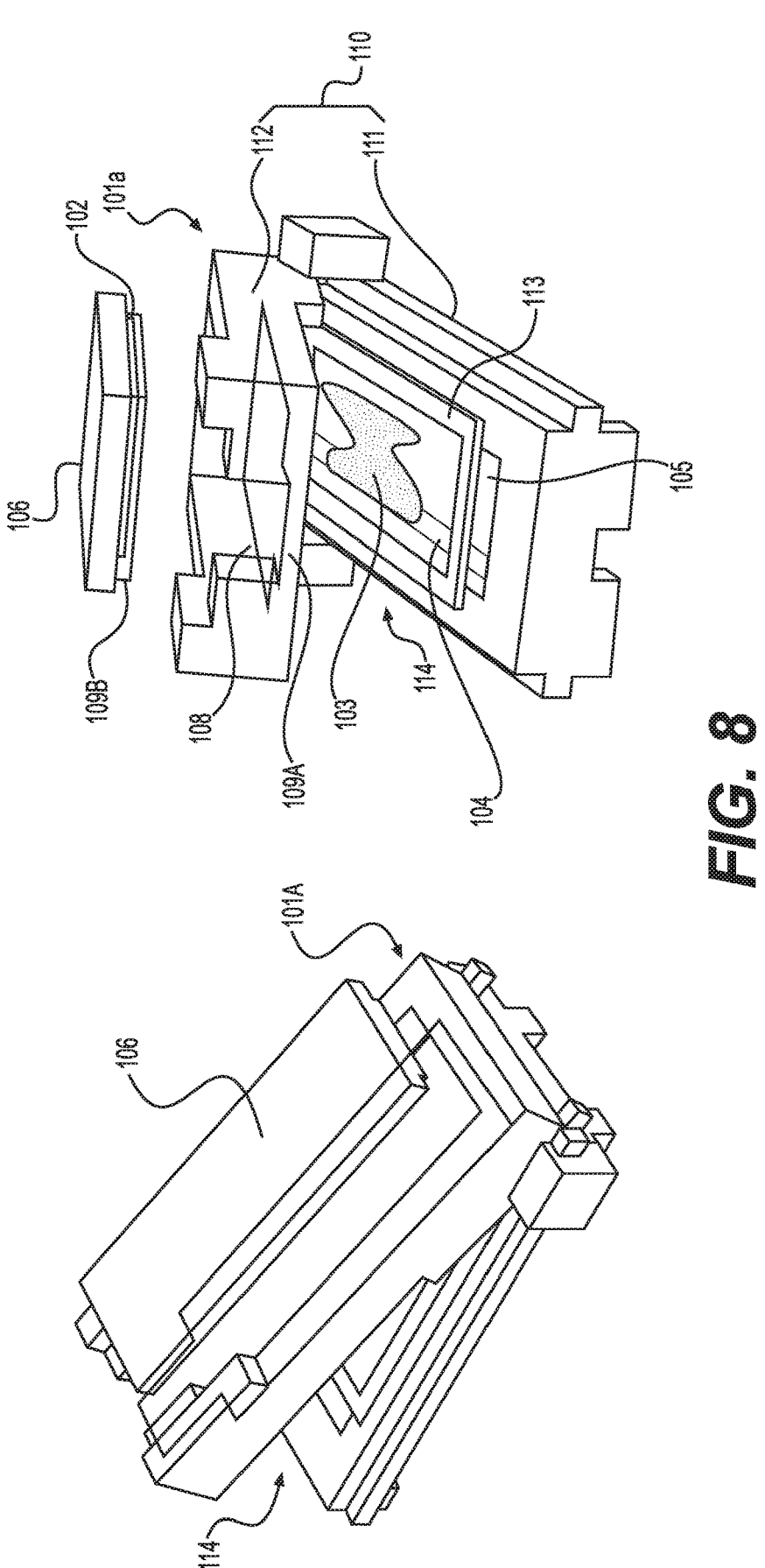
FIG. 8 is a perspective view of the embodiment of a cartridge with a lid that can be opened or removed to give easy access to the underlying film

With reference to FIG. 8, shown are perspective views of an embodiment of an cartridge. The cartridge 101a has a base 110 that includes a bottom plate 111 and a top plate 112. Inside the base 110 is a receptacle 114 that receives a slide 104 on which tissue 103 is disposed. The top plate 112 may be connected to the bottom plate 111 by a hinge or hinged mechanism. The cartridge 101a includes a lid 106 covering the receptacle 114. The lid 106 may be removed or opened from the top plate 112. The embodiment shown in FIG. 8 exemplarily represents the lid 106 that can be removed from the top plate 112. At the front side of the top plate 112, which is an opposite side of the hinged mechanism, the base 110 may have a groove or opening 108, and a lip 109A that may surround the receptacle. The cartridge 101a receives the slide 104 on which tissue 103 is disposed. A film 102 disposed on a lower surface of the lid 106. When the film 102 is placed to cover the slide 104, an edge of the film 102 or pull-tab attached to the edge of the film may be disposed in the opening 108 so that the film can be easily removed after biological sample on the tissue is extracted to the film (see FIGS. 9B and 9D).

The base of the cartridge 101a may have a receptacle to accept a glass slide 104 with human or animal tissue 103 on it. The region below the receptacle has a transparent window 105 that can be fully or partially composed of a material that is transparent (e.g. glass or clear plastic) such that light may be projected by the system or device up through the cartridge and reaches the glass slide and tissue. At the lip 109A of the receptacle, or otherwise surrounding the receptacle (e.g. above or below the lip), there may be a gasket 113, for example composed out of some deformable material that when pressed between two surfaces provides a good vacuum seal. The lid 106 of the cartridge may have a lip or projection 109B facing down, so that when the lid is closed by mechanical, semi-mechanical, manual or robotic means, a vacuum tight seal is created between the base of the cartridge, the deformable gasket, and the lid. This composition of cartridge base, gasket, and lid, providing a vacuum sealed chamber around a glass slide with tissue, may further have at least one port. This port may be in the base of the cartridge, in the lid of the cartridge, or an opening in the gasket, at the front, back, or sides of the cartridge. When the cartridge is placed inside the instrument or device, this port seals up against a connection to an air pump, so that air may be removed from the sealed receptacle in the cartridge. Such removal of air causes the film to press down on the tissue that is on the glass slide. It is further disclosed that the cartridge base and lid may be so designed that the film forms the top part of the vacuum-sealed receptacle, and that this receptacle substantially composed on six sides by the base of the cartridge as the floor, the four walls of the gasket as the sides, and the film as a ceiling, fully encloses the glass slide with tissue. When air is pulled out of the port, the film therefore is pressed by vacuum to cover the tissue on the top of the glass slide, and to everywhere create a good contact between the film and the tissue on top of the glass slide. After application of the light flashes, the film has been activated and the desired parts of the tissue (e.g. all the tumor cells) is attached to the film. Then the cartridge can be opened, by mechanical, semi-mechanical, manual, or robotic means. The lid of the cartridge may have one or multiple components, and one of the components of the lid can open or can be removable so as to provide easy access to the film. The film may then be removed by mechanical, semi-mechanical, manual, or robotic means, for example the film could be peeled off using a tab attached to the film.

With reference to FIGS. 9A-9D, illustrated is a system and method for accessing the film after the film has been activated. The lid 106 of the cartridge 101a may have one or multiple components that can be opened or removed, either manually, semi-manually, by automatic means, or roboti-cally. Doing so can provided added easy access to the underlying film, so that the film 102 can be removed by for example a pull-tab. The film can also be removed by other means, including by manual, semi-manual, automatic, or robotic means. In an embodiment, as shown in FIGS. 9A-9D, the cartridge 101a receives a slide 104 with tissue 103 (see FIG. 9A). The cartridge 101a clamps shut to lay the film 102 on top of the tissue 103. (see FIG. 9B). An edge of the film or pull-tab attached to the film may protrude outwardly beyond the cartridge. However, as described above, when the lid is closed, a vacuum tight seal is created between the base of the cartridge, the deformable gasket, and the lid. A vacuum may be applied through the exit port 107 which presses the film 102 against the tissue 103 (see FIG. 9C). After biological material such as target cells are extracted from the tissue 103, the lid 106 is opened and film 102 with the biological material is removed from the car-tridge 101a (see FIG. 9D).

Figure 10A:
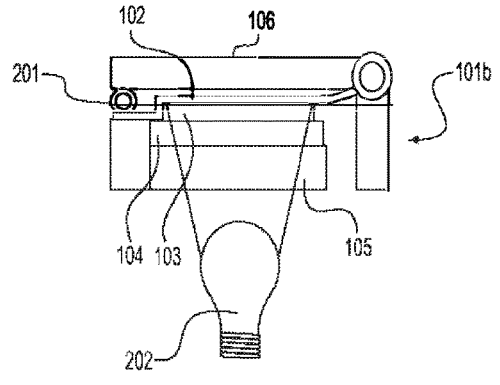
FIG. 10A-10C is a view of a preferred embodiment of cartridge enabling automated removal of a film with tissue from the cartridge and automated removal of tissue cells from the film.
Figure 10B:
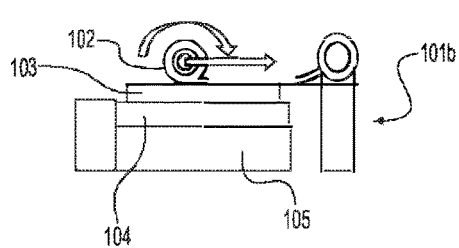
Figure 10C:
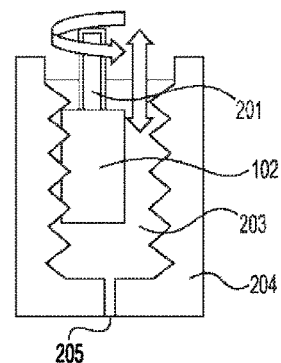

With reference now to FIGS. 10A-10C, illustrated is a system and method for automating release or removal of cells from film. The automated processing system has a rolling pin 201 that is disposed at the edge of the cartridge 101b under the lid 106. The cartridge 101b accepts a glass slide 104 on which a tissue 103 is present, and when the cartridge 101b is clamped shut, the film 102 lays onto the tissue 103 and provides an air-tight space between the transfer film 102 and the air exit port 107. The cartridge 101b has a port 107 enabling a vacuum to be applied to the inside of the cartridge and is air-tight sealed to enable the vacuum seal to be achieved, as described referring to FIGS. 7A-7C. In use, embodiments described herein may extract target cells from tissue samples for down-stream precision molecular testing. Any immunohistochemistry (IHC) stain can be used that stains the target cells dark as compared to non-target cells (Step 1). Such stains are used in the clinical daily, and there are many stains available. After receiving the glass slide 104 on which a tissue sample 103 is present and film 102 is laid on the tissue 103, the rolling pin 201 may press an edge of the film 102. The lid 106 is closed tightly pressing the rolling pin 201, and vacuum is applied through the exit port 107. This vacuum presses the film 102 against the tissue 103 to ensure good thermal contact between the tissue and the film. After the film is then pressed onto the slide on which tissue 103 is present (Step 2), a light bulb 202 is flashed (Step 3, see FIG. 10A). The dark stain absorbs the light and locally heats and melts the film, as a result the film adheres to the stained cells only. Then the film is peeled off by using the rolling pin 201 (Step 4, see FIG. 10B), and the cells on the film 102 are released in solution 203 (Step 5, see FIG. 10C). The whole process is simple and quick, and recovers the target cells with high specificity and efficiency.

The system and method shown in FIGS. 10A-10C may be used to automate Steps 4 and 5 described here. After the a bulb 202 in the instrument flashes to light up through the clear window 105 at the bottom of the cartridge 101b to bind target cells in the tissue 103 to the film 102, the rolling pin 201 peels the transfer film 102 off the slide 104. The peeled film may wrap the rolling pin. This rolling pin does not disrupt the air-tight seal between the film 102 and the vacuum port 107, because the pin is above the film. The embodiment shown uses a rolling pin in the cartridge and a single-use pre-filled serrated vial 204 to release collected material from the film. As shown, after lighted is flashed up through the clear window at the bottom of the cartridge to bind target cells to the film (see FIG. 10A), a rolling pin 201 is applied to peel the film 102 off the slide 104 (see FIG. 10B). Adding this rolling pin does not disrupt the air-tight seal between the film and the vacuum port (discussed with reference to FIGS. 7A-7C), because the pin is above the film. The instrument (automated processing system) trans-lates and rotates the pin (grey arrow) to gently roll the film up. The rolling pin, with the film rolled onto it, is inserted into a single-use pre-filled vial 204 (see FIG. 10C). Having this vial (and the cartridge) be single-use avoids any chance of contamination between patient samples. The pin is moved up and down and rotated against serrated edges of the vial, to break up the film and allow the pre-filled digestion buffer 203 to penetrate into all parts of the film to release the target cells (see FIG. 10C). Mild heat (e.g., 55° C. or another selected temperature) may also be applied. Once maceration and digestion is completed, the fluid that now contains the target material may be let out through an vial exit port 205 at bottom (see FIG. 10C).

In an embodiment, the cartridge uses a single moving part, a rolling pin, to achieve all the steps needed to release the cells from the film. Since the pin is part of the single-use cartridge (the automated system only grasps the base of the pin, without touching the film), and since the pre-filled serrated vial is also single use, there is no chance for cross-contamination from one patient sample to another. Also, the vial is small, not much larger than the pin and film, this reduces the volume of the buffer and provides a con-centrated samples to down-stream instruments (to enable a high signal-to-noise ratio).

Figure 13:
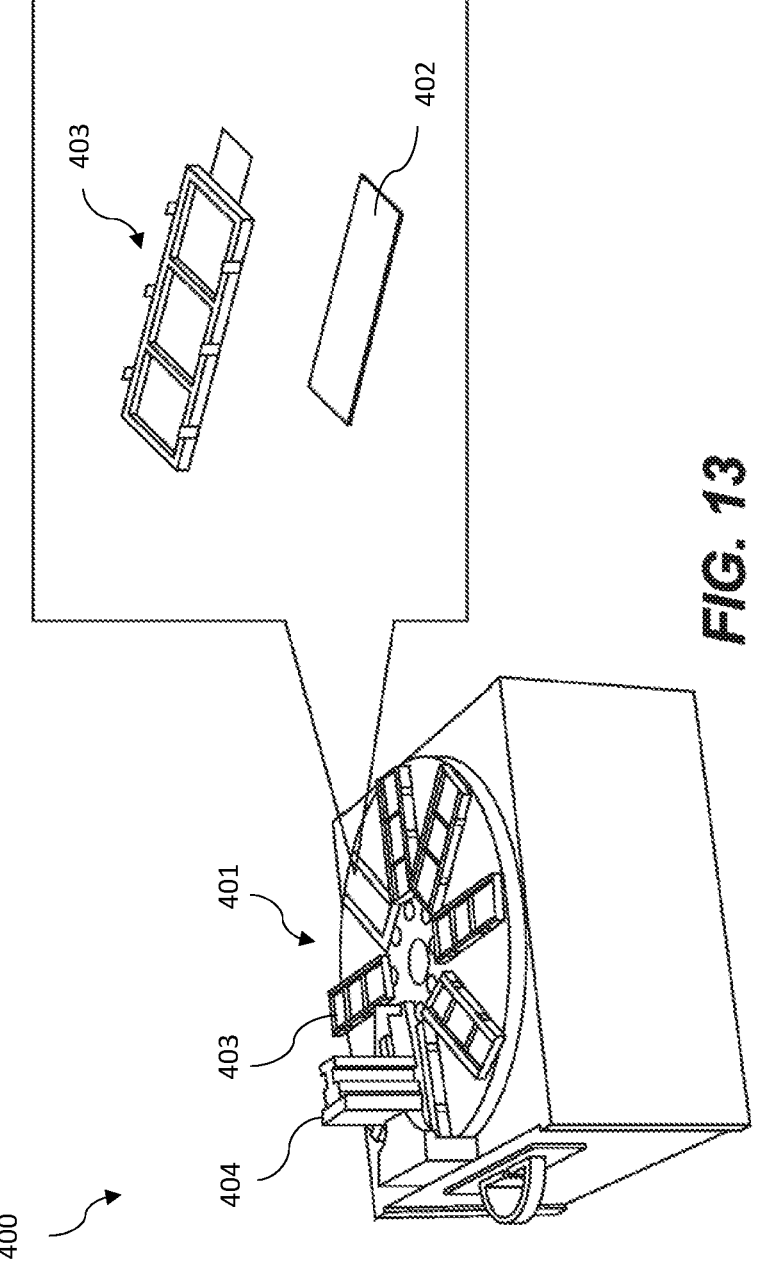
FIG. 13 is a view of a preferred embodiment, which is a cartridge-processing system may be designed as a carousel where cartridges with tissue are entered into horizontal plates.

Referring to FIG. 13, in one preferred embodiment of the invention a cartridge processing system 400 may be designed as a carousel 401 with bases or slots arranged horizontally. In an exemplary embodiment, the slide with biopsy tissue 402 may be placed directly into one of the eight, for example, basses 403 that are fixed to the carousal 401. The consumable is made of three components including cover, film and frame. These may be assembled at the supplier and may be sent to the laboratory. The assembly may be placed on top of the base 403 that already contains the slide. The base 403 with a window and gasket may be fixed to the carousal 401 but can be removed for services. Rotation of the carousel causes each cartridge to be pro-cessed. Cartridges or base containing biological samples may be placed on a carousel designed to convey cartridges in series into a vacuum sealing device 404. After the vacuum sealing process has been applied, the cartridge processing system 400 is then designed to convey the cartridge out of the sealing device, after which the film may be extracted for further processing/analysis as desired by the user.

The methods and systems disclosed herein can be used in part to conduct and improve molecular tests. Activating the film to extract target regions, target cells (e.g. tumor cells), target cellular organelles from tissue samples purifies the molecules that are needed to enable or improve molecular testing. For example, extracting cancer cells from a tissue sample on a glass slide provides purified cancer cells to downstream molecular tests (e.g. to tests such as Oncotype DX for breast cancer, or Neogenomics molecular tests, or many other similar tests). Extracting cancer cells from the sample increases the signal from DNA, RNA, or proteins associated with cancer (increased signal), and decreases the signal not-associated with cancer (since less non-cancer cells are be provided to the molecular test, hence less noise). Thus the methods and systems disclosed herein can provide more material to molecular tests to enable them, and can improve the quality and success of the tests (e.g. by improving the signal-to-noise ratio). In particular, systems and methods disclosed for tissue sample purification can be used to enable and improve outcomes for molecular tests for genetic cancer, for cancer biomarkers, for personalized medicine (tests that select drugs or therapy for cancer or other diseases based on measuring the genetic or proteomic profile of tumors or disease sites).

With reference to FIG. 11, shown is a table including exemplary types of cancers and list of gene mutations for which the methods and systems of the disclosed invention can be used to conduct and improve molecular tests.

The methods and systems of the disclosed invention may be used for molecular tests of cancers and diseases that may include but are not limited to Acute Lymphoblastic Leukemia (ALL), Acute Myeloid Leukemia (AML), Adrenocortical Carcinoma, Childhood Adrenocortical Carcinoma, AIDS-Related Cancers, Kaposi Sarcoma (Soft Tissue Sarcoma), AIDS-Related Lymphoma (Lymphoma), Primary CNS Lymphoma (Lymphoma), Anal Cancer, Appendix Cancer, Astrocytomas, Atypical Teratoid/Rhabdoid Tumor, Basal Cell Carcinoma of the Skin, Bile Duct Cancer, Bladder Cancer, Bone Cancer (includes Ewing Sarcoma and Osteosarcoma and Malignant Fibrous Histiocytoma), Brain Tumors, Breast Cancer, Bronchial Tumors, Burkitt Lymphoma, Carcinoid Tumor (Gastrointestinal), Carcinoma of Unknown Primary, Cardiac (Heart) Tumors, Central Nervous System, Atypical Teratoid/Rhabdoid Tumor, Embryonal Tumors, Germ Cell Tumor, Primary CNS Lymphoma, Cervical Cancer, Cholangiocarcinoma, Chordoma, Chronic Lymphocytic Leukemia (CLL), Chronic Myelogenous Leukemia (CML), Chronic Myeloproliferative Neoplasms, Colorectal Cancer, Craniopharyngioma, Cutaneous T-Cell Lymphoma, Ductal Carcinoma In Situ (DCIS), Embryonal Tumors, Central Nervous System, Endometrial Cancer (Uterine Cancer), Ependymoma, Esophageal Cancer, Esthesioneuroblastoma (Head and Neck Cancer), Ewing Sarcoma (Bone Cancer), Extracranial Germ Cell Tumor, Extragonadal Germ Cell Tumor, Eye Cancer, Intraocular Melanoma, Retinoblastoma, Fallopian Tube Cancer, Fibrous Histiocytoma of Bone, Malignant, and Osteosarcoma, Gallbladder Cancer, Gastric (Stomach) Cancer, Gastrointestinal Carcinoid Tumor, Gastrointestinal Stromal Tumors (GIST) (Soft Tissue Sarcoma), Germ Cell Tumors, Extragonadal Germ Cell Tumors, Ovarian Germ Cell Tumors, Testicular Cancer, Gestational Trophoblastic Disease, Hairy Cell Leukemia, Head and Neck Cancer, Hepatocellular (Liver) Cancer, Histiocytosis, Langerhans Cell, Hodgkin Lymphoma, Hypopharyngeal Cancer (Head and Neck Cancer), Intraocular Melanoma, Islet Cell Tumors, Pancreatic Neuroendocrine Tumors, Kaposi Sarcoma (Soft Tissue Sarcoma), Kidney (Renal Cell) Cancer, Langerhans Cell Histiocytosis, Laryngeal Cancer (Head and Neck Cancer), Leukemia, Lip and Oral Cavity Cancer (Head and Neck Cancer), Liver Cancer, Lung Cancer (Non-Small Cell and Small Cell), Lymphoma, Male Breast Cancer, Malignant Fibrous Histiocytoma of Bone and Osteosarcoma, Melanoma, Melanoma, Intraocular (Eye), Merkel Cell Carcinoma (Skin Cancer), Mesothelioma, Malignant, Metastatic Cancer, Metastatic Squamous Neck Cancer with Occult Primary (Head and Neck Cancer), Midline Tract Carcinoma With NUT Gene Changes, Mouth Cancer (Head and Neck Cancer), Multiple Endocrine Neoplasia Syndromes, Multiple Myeloma/Plasma Cell Neoplasms, Mycosis Fungoides (Lymphoma), Myelodysplastic Syndromes, Myelodysplastic/Myeloproliferative Neoplasms, Myelogenous Leukemia, Chronic (CML), Myeloid Leukemia, Acute (AML), Myeloproliferative Neoplasms, Chronic, Nasal Cavity and Paranasal Sinus Cancer (Head and Neck Cancer), Nasopharyngeal Cancer (Head and Neck Cancer), Neuroblastoma, Non-Hodgkin Lymphoma, Non-Small Cell Lung Cancer, Oral Cancer, Lip and Oral Cavity Cancer and Oropharyngeal Cancer (Head and Neck Cancer), Osteosarcoma and Malignant Fibrous Histiocytoma of Bone, Ovarian Cancer, Pancreatic Cancer, Pancreatic Neuroendocrine Tumors (Islet Cell Tumors), apillomatosis (Childhood Laryngeal), Paraganglioma, Paranasal Sinus and Nasal Cavity Cancer (Head and Neck Cancer), Parathyroid Cancer, Penile Cancer, Pharyngeal Cancer (Head and Neck Cancer), Pheochromocytoma, Pituitary Tumor, Plasma Cell Neoplasm/Multiple Myeloma, Pleuropulmonary Blastoma, Pregnancy and Breast Cancer, Primary Central Nervous System (CNS) Lymphoma, Primary Peritoneal Cancer, Prostate Cancer, Rectal Cancer, Recurrent Cancer, Renal Cell (Kidney) Cancer, Retinoblastoma, Rhabdomyosarcoma, Salivary Gland Cancer (Head and Neck Cancer), Sarcoma, Ewing Sarcoma (Bone Cancer), Kaposi Sarcoma (Soft Tissue Sarcoma), Osteosarcoma (Bone Cancer), Soft Tissue Sarcoma, Uterine Sarcoma, Sezary Syndrome (Lymphoma), Skin Cancer, Small Cell Lung Cancer, Small Intestine Cancer, Soft Tissue Sarcoma, Squamous Cell Carcinoma of the Skin, Squamous Neck Cancer with Occult Primary, Metastatic (Head and Neck Cancer), Stomach (Gastric) Cancer, T-Cell Lymphoma, Cutaneous, Testicular Cancer, Throat Cancer (Head and Neck Cancer), Nasopharyngeal Cancer, Oropharyngeal Cancer, Hypopharyngeal Cancer, Thymoma and Thymic Carcinoma, Thyroid Cancer, Transitional Cell Cancer of the Renal Pelvis and Ureter (Kidney (Renal Cell) Cancer), Ureter and Renal Pelvis, Transitional Cell Cancer (Kidney (Renal Cell) Cancer, Urethral Cancer, Uterine Cancer, Endometrial, Uterine Sarcoma, Vaginal Cancer, Vascular Tumors (Soft Tissue Sarcoma), Vulvar Cancer, and Wilms Tumor and Other Childhood Kidney Tumors.

The methods and systems disclosed herein can use multiple IHC (immunohistochemistry) stains. Disclosed herein is activating film binding to target regions or cells in tissue by light being absorbed by IHC stains. These IHC stains can be any commonly used stain that serves to differentiate target regions and cells in the tissue from non-target regions and cells. Specifically stains for genetic cancers or disease with a genetic component.

Examples of stains include but not limited to A-1-Antichymotrypsin (polyclonal), A-1-Antitrypsin (polyclonal), ACTH (polyclonal), Actin, Muscle Specific (HHF35), Actin, Smooth Muscle (1A4) Mouse Monoclonal Antibody, Actin Muscle (HUC1-1) Primary Antibody, ALK (D5F3) CDx Assay, ALK1 (ALK01) Primary Antibody, Alpha-Fetoprotein Rabbit Polyclonal Antibody, Androgen Receptor (SP107) Rabbit Monoclonal Primary Antibody, Annexin A1 (MRQ-3), anti-S100P (16/f5) Mouse Monoclonal Primary Antibody, Arginase-1 (SP156), Rabbit Monoclonal Primary Antibody, Basal Cell Cocktail (34βE12+p63), 50, Basal Cell Cocktail (34βE12+p63), 250, BCA-225 (Cu-18), bcl-2 (124) Mouse Monoclonal Primary Antibody, bcl-2 (SP66) Rabbit Monoclonal Primary Antibody, bcl-6 (GI191E/A8), Beta-Catenin (14), BG8, Lewisy (F3), BOB.1 (SP92), BRAF V600E (VE1), c-KIT (9.7) Primary Antibody, c-MYC (Y69)

Rabbit Monoclonal Primary Antibody, C3d Rabbit Polyclonal Antibody, C4d (polyclonal), C4d (SP91), CA-125 (0C125), CA19-9 (121SLE), Cadherin 17 (SP183), Rabbit Monoclonal Primary Antibody, Calcitonin (polyclonal), Calcitonin (SP17), Rabbit Monoclonal Primary Antibody, Caldesmon (E89), Calponin-1 (EP798Y), Calretinin (SP65) Rabbit Monoclonal Primary Antibody, Carbonic Anhydrase IX (EP161) Rabbit Monoclonal Primary Antibody, Caveolin-1 (SP43) Rabbit Monoclonal Primary Antibody, CD1a (EP3622), CD2 (MRQ-11), CD3 (2GV6) Rabbit Monoclonal Primary Antibody, CD4 (SP35) Rabbit Monoclonal Primary Antibody, CONFIRM, CD5 (SP19) Rabbit Monoclonal Primary Antibody, CD7 (SP94) Rabbit Monoclonal Primary Antibody, CD8 (SP57) Rabbit Monoclonal Primary Antibody, CD10 (SP67) Rabbit Monoclonal Primary Antibody, CD13 (SP187) Rabbit Monoclonal Primary Antibody, CD14 (EPR3653) Rabbit Monoclonal Antibody, CD15 (MMA) Mouse Monoclonal, Primary Antibody, CD16 (SP175) Rabbit Monoclonal Primary Antibody, CD20 (L26) Primary Antibody, CD21 (2G9), CD21 (EP3093), CD22 (SP104) Rabbit Monoclonal Primary Antibody, CD23 (SP23) Rabbit Monoclonal Primary Antibody, CD25 (4C9), CD30 (Ber-H2) Mouse Monoclonal Primary Antibody, CD31 (JC70), CD33 (SP266) Rabbit Monoclonal Primary Antibody, CD34 (QBEnd/10) Primary Antibody, CD38 (SP149) Rabbit Monoclonal Primary Antibody, CD43 (L60) Mouse Monoclonal Primary Antibody, CD44 (SP37) Rabbit Monoclonal Primary Antibody, CD45 (LCA) (2B11 & PD7/26), CD45, LCA (RP2/18) Primary Antibody, CD45R (MB1), CD45RO (UCHL-1) Primary Antibody, CD56 (123C3) Mouse Monoclonal Primary Antibody, CD56 (MRQ-42), CD57 (NK-1), CD61 (2f2), CD63 (NKI/C3), CD68 (KP-1) Primary Antibody, CD71 (MRQ-48) Mouse Monoclonal Antibody, CD79a (SP18) Rabbit Monoclonal Primary Antibody, CD99 (013) Mouse Monoclonal Primary Antibody, CD138/syndecan-1 (B-A38), CD163 (MRQ-26), CDX-2 (EPR2764Y), CEA (CEA31) Mouse Monoclonal Antibody, CEA (TF 3H8-1) Primary Antibody, Chromogranin A (LK2H10) Primary Antibody, CLDN18 (43-14A) Assay, Collagen Type IV (CIV22), COX-2 (SP21), Cyclin D1 (SP4-R) Rabbit Monoclonal Primary Antibody, Cytokeratin (35betaH11), Cytokeratin (AE1) Primary Antibody, Cytokeratin (CAM 5.2) Mouse Monoclonal Primary Antibody, Cytokeratin 5 (SP27) Rabbit Monoclonal Primary Antibody, Cytokeratin 5/6 (D5/16B4) Mouse Monoclonal Primary Antibody, Cytokeratin 5/14 (EP1601Y/LL002) Rabbit and Mouse Monoclonal Primary Antibody, Cytokeratin 7 (SP52) Rabbit Monoclonal Primary Antibody, Cytokeratin 8 & 18 (B22.1 & B23.1), Cytokeratin 10 (SP99) Rabbit Monoclonal Primary Antibody, Cytokeratin 14 (LL002), Cytokeratin 14 (SP53) Rabbit Monoclonal Primary Antibody, Cytokeratin 17 (SP95) Rabbit Monoclonal Primary Antibody, Cytokeratin 19 (A53-B/A2.26), Cytokeratin 20 (SP33) Rabbit Monoclonal Primary Antibody, Desmin (DE-R-11) Primary Antibody, Desmoglein 3 (5G11) Mouse Monoclonal Primary Antibody, DLL3 (SP347) Assay, DOG1 (SP31) Rabbit Monoclonal Antibody, E-cadherin (36) Mouse Monoclonal Primary Antibody, E-Cadherin (EP700Y), EGFR (3C6) Primary Antibody, EGFR (5B7) Rabbit Monoclonal Primary Antibody, EGFR E746-A750 del (SP111) Rabbit Monoclonal Primary Antibody, EGFR L858R (SP125) Rabbit Monoclonal Primary Antibody, EMA (E29) Mouse Monoclonal Primary Antibody, Ep-CAM (Ber-EP4), Epithelial Related Antigen (MOC-31) Mouse Monoclonal Primary Antibody, ERG (EPR3864) Rabbit Monoclonal Primary Antibody, Estrogen Receptor (ER) (SP1) Rabbit Monoclonal Primary Antibody, Estrogen Receptor (ER) (SP1) Rabbit Monoclonal Primary Antibody, EZH2 (SP129) Rabbit Monoclonal Primary Antibody, Factor VIII-R Ag. (polyclonal), Factor XIIIa (AC-1A1), Factor XIIIa (EP3372), Fascin (55k-2), FITC Albumin Primary Antibody, FITC C1q Primary Antibody, FITC C3 Primary Antibody, FITC Fibrinogen Primary Antibody, FITC IgA Primary Antibody, FITC IgG Primary Antibody, FITC IgM Primary Antibody, FITC Kappa Primary Antibody, FITC Lambda Primary Antibody, Follicular Dendritic Cell, FOXA1 (2F83) Mouse Monoclonal Primary Antibody, FoxP1 (SP133) Rabbit Monoclonal Primary Antibody, FSH (polyclonal), Galectin-3 (9C4), Gastrin (polyclonal), GATA3 (L50-823) Mouse Monoclonal Primary Antibody, GCDFP-15 (EP1582Y) Rabbit Monoclonal Antibody, GH (polyclonal), Glial Fibrillary Acidic Protein (GFAP) (EP672Y), Glucagon Rabbit Polyclonal Primary Antibody, GLUT1 Rabbit Polyclonal Antibody, Glutamine Synthetase (GS-6) Mouse Monoclonal Primary Antibody, Glycophorin A (GA-R2), Glypican-3 (1G12), Glypican 3 (GC33) Mouse Monoclonal Primary Antibody, Granzyme B (polyclonal), HA Assay, HBME-1 (HBME-1), hCG (polyclonal), *Helicobacter pylori* (SP48) Rabbit Monoclonal Primary Antibody, *Helicobacter pylori* (SP48) Rabbit Monoclonal Primary Antibody, Hemoglobin A (SP212) Rabbit Monoclonal Primary Antibody, Hepatocyte Specific Antigen (OCH1E5), HER-2/neu (4B5) Rabbit Monoclonal Primary Antibody, HGAL (MRQ-49) Mouse Monoclonal Antibody, Human Equilibrative Nucleoside Transporter 1 (SP120) Rabbit Monoclonal Primary Antibody, Human Placental Lactogen (hPL)(polyclonal), IgA (polyclonal), IgD (polyclonal), IGF-1R (G11) Rabbit Monoclonal Primary Antibody, IgG (polyclonal), IgG4 (MRQ-44) Mouse Monoclonal Antibody, IgM (polyclonal), Inhibin, alpha (MRQ-63) Rabbit Monoclonal Primary Antibody, Inhibin, alpha (R1), INI-1 (MRQ-27) Mouse Monoclonal Primary Antibody, Kappa Rabbit Polyclonal Primary Antibody, Keratin (34BE12) Mouse Monoclonal Primary Antibody, Keratin (AE3) Primary Antibody, Ki-67 (30-9) Rabbit Monoclonal Primary Antibody, Ksp-cadherin (MRQ-33), Lambda Rabbit Polyclonal Primary, LH (polyclonal), LMO2 (1A9-1) Mouse Monoclonal Primary Antibody, LMO2 (SP51), Lysozyme (polyclonal), Macrophage (HAM-56), Mammaglobin (31A5), MART-1/melan A (A103) Mouse Monoclonal Primary Antibody, Melanoma Associated Antigen (KBA.62) Mouse Monoclonal Antibody, Melanoma Associated Antigen (PNL2) Mouse Monoclonal Antibody, Melanoma Triple Cocktail (HMB45+A103+T311) Primary Antibody, Melanosome (HMB45) Mouse Monoclonal Primary Antibody, MITF (C5/D5) Mouse Monoclonal Primary Antibody, MLH1 (M1), MSH2 (G219-1129), MSH6 (SP93), MSLN (SP74) Assay, MUC1 (H23) Mouse Monoclonal Primary Antibody, MUC2 (MRQ-18), MUCSAC (MRQ-19), MUC6 (MRQ-20), MUM1 (EP190) Rabbit Monoclonal Primary Antibody, MUM1 (MRQ-43), Myeloperoxidase (polyclonal), MyoD1 (EP212) Rabbit Monoclonal Primary Antibody, Myogenin (F5D), Myoglobin (polyclonal), Myosin, Smooth Muscle (SMMS-1), Napsin A (MRQ-60) Mouse Monoclonal Primary Antibody, Napsin A (polyclonal), Negative Control (Monoclonal), Negative Control Rabbit Ig, Nerve Growth Factor Receptor (NGFR) (MRQ-21), Neurofilament (2F11), Neutrophil Elastase (SP203) Rabbit Monoclonal Primary Antibody, NKX3.1 (EP356) Rabbit Monoclonal Primary Antibody, NSE (MRQ-55) Mouse Monoclonal Primary Antibody, Oct-2 (MRQ-2), Oct-4 (MRQ-10), Olig2 (EP112) Rabbit Monoclonal Primary Antibody, p21WAF1 (DCS-60.2), p27Kip1 (SX53G8), p40 (BC28) Mouse Monoclonal Primary Antibody, p53 (Bp53-11) Primary Antibody, p53

(DO-7) Primary Antibody, p57Kip2 (Kp10) Mouse Monoclonal Primary Antibody, p63 (4A4) Mouse Monoclonal Primary Antibody, p120 catenin (98) Mouse Monoclonal Primary Antibody, p504s (SP116) Rabbit Monoclonal Primary Antibody, pan-TRK (EPR17341) Assay, Pan Keratin (AE1/AE3/PCK26) Primary Antibody, Pan Keratin (AE1/AE3/PCK26) Primary Antibody, Parathyroid Hormone (PM) (MRQ-31) Mouse Monoclonal Antibody, PAX-8 (MRQ-50), PAXS (SP34) Rabbit Monoclonal Primary Antibody, PD-1 (NAT105) Mouse Monoclonal Antibody, PD-L1 (SP142) Assay, PD-L1 (SP263) Assay, PD-L1 (SP263) Rabbit Monoclonal Primary Antibody, Perforin (MRQ-23), PGP 9.5 Rabbit Polyclonal Antibody, Phosphohistone H3 (PHH3), PLAP (NB10), PMS2 (A16-4), Podoplanin (D2-40) Mouse Monoclonal Antibody, Progesterone Receptor (PR) (1E2) Rabbit Monoclonal Primary Antibody, Progesterone Receptor (PR) (1E2) Rabbit Monoclonal Primary Antibody, Prolactin (polyclonal), Prostate Specific Antigen (PSA) Rabbit Polyclonal Primary Antibody, PSA (ER-PR8), PSAP (PASE/4LJ), PSMA (EP192) Rabbit Monoclonal Primary Antibody, PTEN (SP218) Rabbit Monoclonal Primary Antibody, Rabbit Monoclonal Negative Control Ig, Renal Cell Carcinoma (PN-15), ROS1 (SP384) Rabbit Monoclonal Primary Antibody, S100 (4C4.9) Primary Antibody, S100 (Polyclonal) Primary Antibody, SALL4 (6E3) Mouse Monoclonal Primary Antibody, Smoothelin (R4A) Mouse Monoclonal Antibody, Somatostatin (polyclonal), SOX-2 (SP76), SOX-10 (SP267) Rabbit Monoclonal Primary Antibody, SOX-11 (MRQ-58) Mouse Monoclonal Primary Antibody, Spectrin (RBC2/3D5), Synaptophysin (MRQ-40) Rabbit Monoclonal Antibody, Synaptophysin (SP11) Rabbit Monoclonal Primary Antibody, T-bet (MRQ-46) Rabbit Monoclonal Antibody, TAG-72 (B72.3), TdT (polyclonal), TFE3 (MRQ-37) Rabbit Monoclonal Primary Antibody, TFF3 (7F1.21) Mouse Monoclonal Primary Antibody, Thymidine Phosphorylase (P-GF.44C) Mouse Monoclonal Primary Antibody, Thyroglobulin (2H11+6E1), Thyroid Transcription Factor-1 (8G7G3/1) Mouse Monoclonal Primary Antibody, Thyroid Transcription Factor-1 (SP141) Rabbit Monoclonal Primary Antibody, Topoisomerase Ha (JS5B4) Rabbit Monoclonal Primary Antibody, Total c-MET (SP44) Rabbit Monoclonal Primary Antibody, TRAcP (9C5) Mouse Monoclonal Primary Antibody, Tryptase (G3), TSH (polyclonal), Tyrosinase (T311) Mouse Monoclonal Primary Antibody, Uroplakin III (SP73) Rabbit Monoclonal Antibody, Villin (CWWB1), Vimentin (V9) Primary Antibody, Vimentin (Vim 3B4) Primary Antibody, WT1 (6F-H2), and ZAP-70 (2F3.2).

The methods and systems of the disclosed invention may be used for molecular tests for cardiovascular genetic diseases, infectious diseases, Alzheimer's Disease, and diabetes. The infectious diseases may include but are not limited to Malaria, Mycobacterial Diseases (leprosy and tuberculosis), and Viral Diseases (HIV/AIDS, hepatitis B or hepatitis C virus). The cardiovascular genetic diseases may include but are not limited to Inherited heart diseases, commonly known as genetic heart disease, hypertrophic, restrictive, arrhythmogenic right ventricular, and dilated cardiomyopathies, inherited heart rhythm disorders such as LongQT and Brugada syndromes, familial cardiac amyloid, and other inherited cardiac conditions.

The methods and systems disclosed can also be combined with histological and pathology or biopsy imaging capabilities. In particular, the tissue samples can be imaged before and after region/cell extraction, to record the histology, morphology, or image of the tissue before extraction of regions, and after. Both the tissue that remains on the slide can be recorded, and the tissue that is extracted by the film can be imaged and recorded (either by photographing the film while it is still attached to the lid of the cartridge, or after the film has been removed, or by the process of subtraction meaning image on the film is original image minus the image of what has remained after extraction). Commonly used imaging platforms can be attached to or combined with the disclosed systems and methods, as an integrated component, as an attached module, or as a downstream capability.

Figure 12:
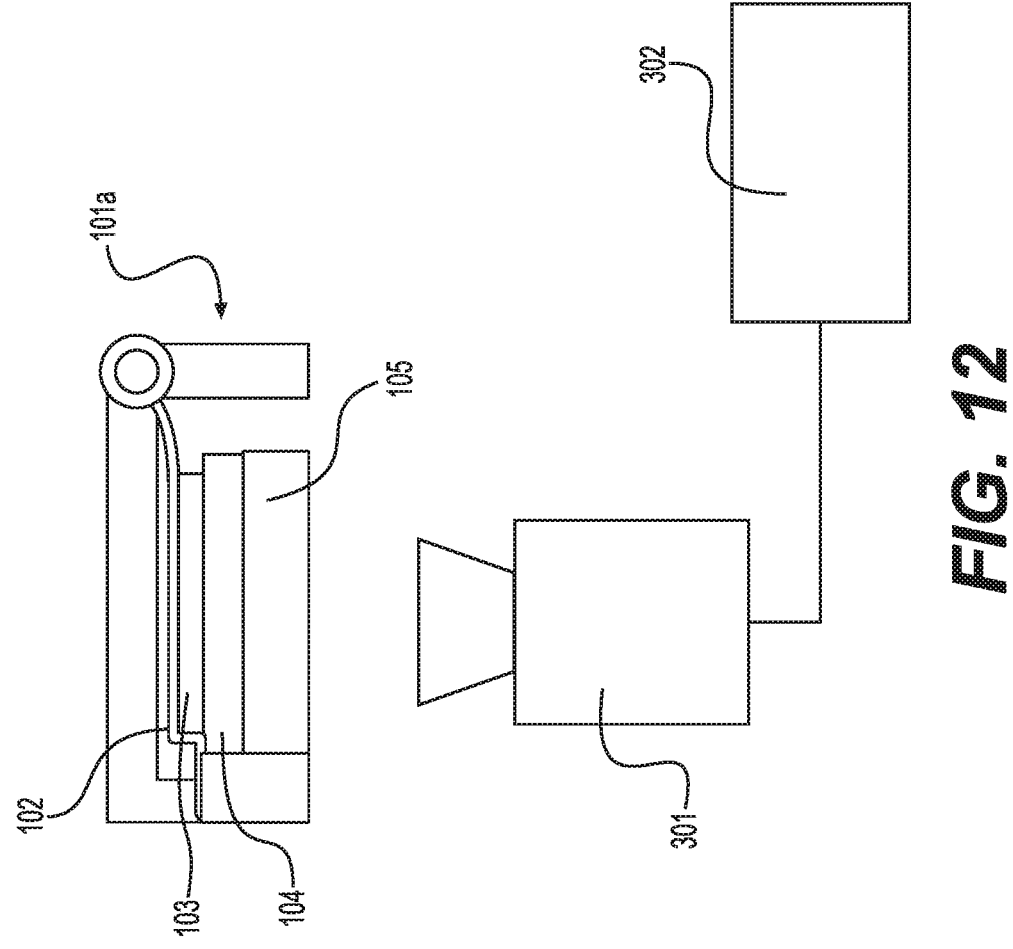
FIG. 12 is a view of an exemplary imaging system photographing the film inside the cartridge of the embodiment of the disclosed invention.

With reference to FIG. 12, shown is an exemplary imaging system photographing the film inside the cartridge 101, 101a or 101b. An imaging system 301 is placed facing the transparent window 105 and is connected to an image control system 302 that controls operations of the imaging system 301 and may collect images captured by the imaging system 301. The imaging system may include any commonly used imaging platforms such as still image cameras and video cameras.

Embodiments include a method for molecular tests of one or more biological materials. The method includes mounting a tissue on a slide, in which the tissue includes the one or more biological materials, loading the slide having the tissue in a receptacle of a cartridge that contains a film disposed on an inner surface of a lid of the cartridge, in which the film is suitable to extract the one or more biological materials from the tissue, pressing the film against the tissue mounted on the slide, in which the tissue or at least a portion of the tissue adheres to the film, removing the film from the cartridge, and extracting the one or more biological materials from the tissue. In embodiments, pressing the film includes applying vacuum suction through a port of the cartridge to press the film against the tissue on the slide and removing the film includes removing the film by using a pull-tab attached to the film. Embodiments may further include ending the pressing the film against the tissue. The film and tissue may be illuminated with light through a transparent window of the cartridge and the tissue may be stained by immunohistochemistry (IHC). Likewise, removing the film may include rolling a rolling pin on the film to roll-up and peel the film off the tissue and extracting the one or more biological materials may include inserting the rolling pin having the peeled film into a container filled with digestion buffer and agitating the rolling pin with the peeled film in the digestion buffer. Material of the film may include polymer, polystyrene, wax, rubber, silicon, silicone, paper, cloth, metal, alloys, an impregnated web, or a liquid material that dries or otherwise hardens to form a flexible, semiflexible, or rigid covering and the slide may be a glass slide. The method may include performing molecular tests on the extracted one or more biological materials and the molecular tests may include tests for genetic cancers, cancer biomarkers, cardiovascular diseases, infectious diseases, Alzheimer's disease, or diabetes. The one or more biological materials may include cancer cells, DNA associated with cancer, RNA associated with cancer, or protein associated with cancer and the tissue may include immunohistochemistry (IHC) stains, stains for generic cancers, stains for cancer biomarkers, stains for cardiovascular diseases, or stains for infectious diseases.

Embodiments include a cartridge processing system for molecular tests that include extracting one or more biological materials from tissues. The cartridge processing system includes a table top platform, a lid disposed on the table top platform, and a film disposed on an inner surface of the lid between the lid and the table top platform, in which the film is suitable to extract the one or more biological materials from the tissues, and one or more slides, on which tissues are disposed, are placed on the table top platform, and the film covers the one or more slides. The table top platform may include a transparent portion. The cartridge processing system may further include a lamp or flash bulb to illuminate the film and tissues through the transparent portion of the table top platform. The cartridge processing system may further include an imaging system to photograph the film and tissues through the transparent portion of the table top platform.

The foregoing descriptions of specific embodiments of the present invention have been presented for purposes of illustration and description. They are not intended to be exhaustive or to limit the invention and method of use to the precise forms disclosed. Obviously many modifications and variations are possible in light of the above teaching. It is understood that various omissions or substitutions of equivalents are contemplated as circumstance may suggest or render expedient, but is intended to cover the application or implementation without departing from the spirit or scope of the claims of the present invention.

What is claimed is:

1. A cartridge processing system for molecular tests that include extracting one or more biological materials from a tissue, comprising:
    a sealing device;
    one or more cartridges; and
    a carousel that contains the one or more cartridges and allows each cartridge to be delivered into the sealing device, wherein the sealing device applies vacuum suction to the cartridge placed in the sealing device, and each cartridge comprises:
        a base having a receptacle inside the base, wherein the base comprises a transparent window placed under the receptacle, and the receptacle contains a slide on which the tissue is disposed;
        a solid lid placed over the receptacle and entirely covering the receptacle;
        a film disposed between the lid and the tissue, wherein a portion of the film, which covers the tissue, entirely contacts an inner surface of the lid, and the film is suitable to extract the one or more biological materials from the tissue; and
        a gasket in the base to surround the slide, wherein the lid creates a sealed chamber around the gasket that encloses the slide, and vacuum suction is applied through a port of the base to press the film against the tissue on the slide.

2. The cartridge processing system of claim 1 further comprising a lamp or flash bulb to illuminate the film and tissue through the transparent window of the cartridge placed in the sealing device.

3. The cartridge processing system of claim 1 further comprising an imaging system to photograph the film and tissue through the transparent window of the cartridge placed in the sealing device.

4. A cartridge processing system for molecular tests that include extracting one or more biological materials from a tissue, comprising:
    a table top platform;
    a lid disposed on the table top platform; and
    one or more cartridges disposed between the table top platform and the lid, wherein each of the one or more cartridges comprises:
        a base having a receptacle inside the base, wherein the base comprises a transparent window placed under the receptacle, and the receptacle contains a slide on which the tissue is disposed;
        a solid lid placed over the receptacle and entirely covering the receptacle;
        a film disposed between the lid and the tissue, wherein a portion of the film, which covers the tissue, entirely contacts an inner surface of the lid, and the film is suitable to extract the one or more biological materials from the tissue; and
        a gasket in the base to surround the slide, wherein the lid creates a sealed chamber around the gasket that encloses the slide, and vacuum suction is applied through a port of the base to press the film against the tissue on the slide.

5. The cartridge processing system of claim 4 wherein the table top platform includes a transparent portion.

6. The cartridge processing system of claim 5 further comprising a lamp or flash bulb to illuminate the film and tissue through the transparent portion of the table top platform and through the transparent window of the cartridge.

7. The cartridge processing system of claim 5 further comprising an imaging system to photograph the film and tissue through the transparent portion of the table top platform and through the transparent window of the cartridge placed in a sealing device.

* * * * *